US011472862B2

(12) United States Patent
Casal Alvarez et al.

(10) Patent No.: US 11,472,862 B2
(45) Date of Patent: Oct. 18, 2022

(54) IL13Rα2 PEPTIDE AND ITS USES

(71) Applicant: CONSEJO SUPERIOR DE INVESTIGACIONES CIENTÍFICAS, Madrid (ES)

(72) Inventors: Jose Ignacio Casal Alvarez, Madrid (ES); Rubén Álvaro Bartolomé Conde, Madrid (ES)

(73) Assignee: CONSEJO SUPERIOR DE INVESTIGACIONES CIENTÍFICAS, Madrid (ES)

( * ) Notice: Subject to any disclaimer, the term of this patent is extended or adjusted under 35 U.S.C. 154(b) by 36 days.

(21) Appl. No.: 16/975,582

(22) PCT Filed: Nov. 5, 2018

(86) PCT No.: PCT/EP2018/080193
§ 371 (c)(1),
(2) Date: Aug. 25, 2020

(87) PCT Pub. No.: WO2019/086676
PCT Pub. Date: May 9, 2019

(65) Prior Publication Data
US 2021/0363224 A1 Nov. 25, 2021

(30) Foreign Application Priority Data
Nov. 3, 2017 (EP) ..................................... 17382737

(51) Int. Cl.
*C07K 14/715* (2006.01)
*A61P 35/04* (2006.01)
*A61K 38/00* (2006.01)

(52) U.S. Cl.
CPC .......... *C07K 14/7155* (2013.01); *A61P 35/04* (2018.01); *A61K 38/00* (2013.01)

(58) Field of Classification Search
None
See application file for complete search history.

(56) References Cited

U.S. PATENT DOCUMENTS 7,338,929 B2 * 3/2008 Debinski ................. A61P 43/00
424/185.1

FOREIGN PATENT DOCUMENTS

| KR | 20130011056 A | 1/2013 |
|----|---------------|--------|
| WO | 0158479 A1 | 8/2001 |
| WO | 0177332 A2 | 10/2001 |
| WO | 03092717 A1 | 11/2003 |
| WO | 2009079790 A1 | 7/2009 |

OTHER PUBLICATIONS

Sattiraju et al., "IL13RA2 targeted alpha particle therapy against glioblastomas", Impact Journals, Oncotarget, vol. 8, Issue No. 26, 2017, pp. 42997-43007, 11 pages.
Altschul et al., "Basic Local Alignment Search Tool", Journal Molecular Biology, Academic Press Limited, 1990, vol. No. 215, pp. 403-410, 8 pages.
Popovic et al., "Structural Characterisation Reveals Mechanism of IL-13-Neutralising Monoclonal Antibody Tralokinumab as Inhibition of Binding to IL-13Rα1 and IL-13Rα2", Journal Molecular Biology, 2017, vol. No. 429, pp. 208-219, 12 pages.
Gour & Wills-Karp, "IL-4 and IL-13 signaling in allergic airway disease", Cytokine, Elsevier, Science Direct, vol. No. 75, Issue No. 1, Sep. 2015, pp. 68-78, 11 pages.
Puri et al., "Targeting of Interleukin-13 Receptor on Human Renal Cell Carcinoma Cells by a Recombinant Chimeric Protein Composed of Interleukin-13 and a Truncated Form of Pseudomonas Exotoxin A (PE38QQR)", Blood, vol. No. 87, Issue No. 10, May 1996, pp. 4333-4339, 7 pages.
Prades et al., "Applying the Retro-Enantio Approach to Obtain a Peptide Capable of Overcoming the Blood-Brain Barrier", Wiley Online Library, Angewandte Chemistry International Edition, 2015, vol. No. 54, pp. 3967-3972, 6 pages.
Balyasnikova et al., "Characterization and Immunotherapeutic Implications for a Novel Antibody Targeting Interleukin (IL)-13 Receptor α2", Journal of Biological Chemistry, The American Society for Biochemistry and Molecular Biology, Inc., vol. No. 287, Issue No. 36, Aug. 31, 2012, pp. 30215-30227, 14 pages.
Mentink-Kane & Wynn, "Opposing roles for IL-13 and IL-13 receptor α2 in health and disease", Blackwell Munksgaard, Immunological Reviews, 2004, vol. No. 202, pp. 191-202, 12 pages.
Kunwar et al., "Phase III randomized trial of CED of IL13-PE38QQR vs Gliadel wafers for recurrent glioblastoma†", Oxford University Press, Society for Neuro-Oncology, Neuro-Oncology, 2010, vol. No. 12, Issue No. 8, pp. 871-881, 11 pages.
Joshi et al., "Human Adrenomedullin Up-regulates Interleukin-13 Receptor α2 Chain in Prostate Cancer In vitro and In vivo: A Novel Approach to Sensitize Prostate Cancer to Anticancer Therapy", AACR Publications, the American Association for Cancer Research, 2008, vol. No. 68, Issue No. 22, 8 pages.
Gao et al., "Ligand modified nanoparticles increases cell uptake, alters endocytosis and elevates glioma distribution and internalization", Scientific Reports, 2013, vol. No. 3, Issue No. 2534, 8 pages.
Arthur G. Street, "Intrinsic b-sheet propensities result from van der Waals interactions between side chains and the local backbone", Journal, 1999, pp. 9074-9076, vol. 96, Proceedings of the National Academy of Sciences of the United States of America—Biophysics.
Patrick J. Lupardus, "Molecular basis for shared cytokine recognition revealed in the structure of an unusually high affinity complex between IL-13 and IL-13Rα2", Journal, 2010, pp. 1-22, vol. 18, No. 3, Structure.
Kazuo Fujiwara, "Dependence of α-helical and β-sheet amino acid propensities on the overall protein fold type", Journal, 2012, pp. 1-15, vol. 12, No. 18, BMC Structural Biology.

* cited by examiner

*Primary Examiner* — Ronald T Niebauer
(74) *Attorney, Agent, or Firm* — Hayes Soloway PC

(57) ABSTRACT

The invention relates to a peptide comprising the amino acid sequence SEQ ID NO: 1 or a variant thereof capable of inhibiting IL13/IL13Rα2 signalling. The invention also relates to a fusion protein, nanoparticle, virus-like particle and pharmaceutical composition comprising said peptide, and to their use for treating a cancer characterized by having increased expression of IL13Rα2, or for treating asthma, atopic dermatitis or fibrosis, or for preventing the metastatic progression of a cancer characterized by having increased expression of IL13Rα2.

12 Claims, 11 Drawing Sheets

Specification includes a Sequence Listing.

A

B

C

SEQUENCE LISTING

<160> NUMBER OF SEQ ID NOS: 22

<210> SEQ ID NO 1
<211> LENGTH: 8
<212> TYPE: PRT
<213> ORGANISM: Artificial Sequence
<220> FEATURE:
<223> OTHER INFORMATION: Peptide derived from IL13Ralpha2

<400> SEQUENCE: 1

Trp Lys Thr Ile Ile Thr Lys Asn
1               5

<210> SEQ ID NO 2
<211> LENGTH: 8
<212> TYPE: PRT
<213> ORGANISM: Artificial Sequence
<220> FEATURE:
<223> OTHER INFORMATION: Inhibitory peptide of IL13/IL13Ralpha2
      signalling
<220> FEATURE:
<221> NAME/KEY: VARIANT
<222> LOCATION: (1)..(1)
<223> OTHER INFORMATION: /replace="Phe" /replace="Tyr"
<220> FEATURE:
<221> NAME/KEY: VARIANT
<222> LOCATION: (2)..(2)
<223> OTHER INFORMATION: /replace="Arg"
<220> FEATURE:
<221> NAME/KEY: VARIANT
<222> LOCATION: (3)..(3)
<223> OTHER INFORMATION: /replace="Ser"
<220> FEATURE:
<221> NAME/KEY: VARIANT
<222> LOCATION: (4)..(4)
<223> OTHER INFORMATION: /replace="Ala" /replace="Leu" /replace="Met"
      /replace="Val"
<220> FEATURE:
<221> NAME/KEY: VARIANT
<222> LOCATION: (5)..(5)
<223> OTHER INFORMATION: /replace="Leu" /replace="Met" /replace="Val"
<220> FEATURE:
<221> NAME/KEY: VARIANT
<222> LOCATION: (6)..(6)
<223> OTHER INFORMATION: /replace="Ser"
<220> FEATURE:
<221> NAME/KEY: VARIANT
<222> LOCATION: (7)..(7)
<223> OTHER INFORMATION: /replace="Ala" /replace="Arg"

-continued

```
<220> FEATURE:
<221> NAME/KEY: VARIANT
<222> LOCATION: (8)..(8)
<223> OTHER INFORMATION: /replace="Gln"

<400> SEQUENCE: 2

Trp Lys Thr Ile Ile Thr Lys Asn
1               5

<210> SEQ ID NO 3
<211> LENGTH: 12
<212> TYPE: PRT
<213> ORGANISM: Artificial Sequence
<220> FEATURE:
<223> OTHER INFORMATION: Inhibitory peptide of IL13/IL13Ralpha2
      signaling

<400> SEQUENCE: 3

Gly Ser Glu Thr Trp Lys Thr Ile Ile Thr Lys Asn
1               5                   10

<210> SEQ ID NO 4
<211> LENGTH: 8
<212> TYPE: PRT
<213> ORGANISM: Artificial Sequence
<220> FEATURE:
<223> OTHER INFORMATION: Inhibitory peptide of IL13/IL13Ralpha2
      signaling

<400> SEQUENCE: 4

Trp Lys Thr Ala Ile Thr Ala Asn
1               5

<210> SEQ ID NO 5
<211> LENGTH: 8
<212> TYPE: PRT
<213> ORGANISM: Artificial Sequence
<220> FEATURE:
<223> OTHER INFORMATION: Inhibitory peptide of IL13/IL13Ralpha2
      signaling

<400> SEQUENCE: 5

Trp Arg Thr Ile Ile Thr Lys Asn
1               5

<210> SEQ ID NO 6
<211> LENGTH: 8
<212> TYPE: PRT
<213> ORGANISM: Artificial Sequence
<220> FEATURE:
<223> OTHER INFORMATION: Inhibitory peptide of IL13/IL13Ralpha2
      signaling

<400> SEQUENCE: 6

Trp Lys Thr Ile Ile Thr Arg Asn
1               5

<210> SEQ ID NO 7
<211> LENGTH: 8
<212> TYPE: PRT
<213> ORGANISM: Artificial Sequence
<220> FEATURE:
<223> OTHER INFORMATION: Inhibitory peptide of IL13/IL13Ralpha2
      signaling

<400> SEQUENCE: 7

Trp Lys Thr Val Ile Thr Lys Asn
1               5
```

```
<210> SEQ ID NO 8
<211> LENGTH: 8
<212> TYPE: PRT
<213> ORGANISM: Artificial Sequence
<220> FEATURE:
<223> OTHER INFORMATION: Inhibitory peptide of IL13/IL13Ralpha2
      signaling

<400> SEQUENCE: 8

Trp Lys Thr Ile Val Thr Lys Asn
1               5

<210> SEQ ID NO 9
<211> LENGTH: 380
<212> TYPE: PRT
<213> ORGANISM: Homo sapiens

<400> SEQUENCE: 9

Met Ala Phe Val Cys Leu Ala Ile Gly Cys Leu Tyr Thr Phe Leu Ile
1               5                   10                  15

Ser Thr Thr Phe Gly Cys Thr Ser Ser Asp Thr Glu Ile Lys Val
            20                  25                  30

Asn Pro Pro Gln Asp Phe Glu Ile Val Asp Pro Gly Tyr Leu Gly Tyr
        35                  40                  45

Leu Tyr Leu Gln Trp Gln Pro Pro Leu Ser Leu Asp His Phe Lys Glu
    50                  55                  60

Cys Thr Val Glu Tyr Glu Leu Lys Tyr Arg Asn Ile Gly Ser Glu Thr
65                  70                  75                  80

Trp Lys Thr Ile Ile Thr Lys Asn Leu His Tyr Lys Asp Gly Phe Asp
                85                  90                  95

Leu Asn Lys Gly Ile Glu Ala Lys Ile His Thr Leu Leu Pro Trp Gln
            100                 105                 110

Cys Thr Asn Gly Ser Glu Val Gln Ser Ser Trp Ala Glu Thr Thr Tyr
        115                 120                 125

Trp Ile Ser Pro Gln Gly Ile Pro Glu Thr Lys Val Gln Asp Met Asp
    130                 135                 140

Cys Val Tyr Tyr Asn Trp Gln Tyr Leu Leu Cys Ser Trp Lys Pro Gly
145                 150                 155                 160

Ile Gly Val Leu Leu Asp Thr Asn Tyr Asn Leu Phe Tyr Trp Tyr Glu
                165                 170                 175

Gly Leu Asp His Ala Leu Gln Cys Val Asp Tyr Ile Lys Ala Asp Gly
            180                 185                 190

Gln Asn Ile Gly Cys Arg Phe Pro Tyr Leu Glu Ala Ser Asp Tyr Lys
        195                 200                 205

Asp Phe Tyr Ile Cys Val Asn Gly Ser Ser Glu Asn Lys Pro Ile Arg
    210                 215                 220

Ser Ser Tyr Phe Thr Phe Gln Leu Gln Asn Ile Val Lys Pro Leu Pro
225                 230                 235                 240

Pro Val Tyr Leu Thr Phe Thr Arg Glu Ser Ser Cys Glu Ile Lys Leu
                245                 250                 255

Lys Trp Ser Ile Pro Leu Gly Pro Ile Pro Ala Arg Cys Phe Asp Tyr
            260                 265                 270

Glu Ile Glu Ile Arg Glu Asp Asp Thr Thr Leu Val Thr Ala Thr Val
        275                 280                 285

Glu Asn Glu Thr Tyr Thr Leu Lys Thr Thr Asn Glu Thr Arg Gln Leu
    290                 295                 300
```

```
Cys Phe Val Val Arg Ser Lys Val Asn Ile Tyr Cys Ser Asp Asp Gly
305                 310                 315                 320

Ile Trp Ser Glu Trp Ser Asp Lys Gln Cys Trp Glu Gly Glu Asp Leu
                325                 330                 335

Ser Lys Lys Thr Leu Leu Arg Phe Trp Leu Pro Phe Gly Phe Ile Leu
                340                 345                 350

Ile Leu Val Ile Phe Val Thr Gly Leu Leu Leu Arg Lys Pro Asn Thr
                355                 360                 365

Tyr Pro Lys Met Ile Pro Glu Phe Phe Cys Asp Thr
                370                 375                 380
```

```
<210> SEQ ID NO 10
<211> LENGTH: 12
<212> TYPE: PRT
<213> ORGANISM: Artificial Sequence
<220> FEATURE:
<223> OTHER INFORMATION: Inhibitory peptide of IL13/IL13Ralpha2
      signaling
<220> FEATURE:
<221> NAME/KEY: VARIANT
<222> LOCATION: (5)..(5)
<223> OTHER INFORMATION: Xaa can be selected from: Trp, Phe or Tyr
<220> FEATURE:
<221> NAME/KEY: VARIANT
<222> LOCATION: (6)..(6)
<223> OTHER INFORMATION: Xaa can be selected from: Lys or Arg
<220> FEATURE:
<221> NAME/KEY: VARIANT
<222> LOCATION: (7)..(7)
<223> OTHER INFORMATION: Xaa can be selected from: Thr or Ser
<220> FEATURE:
<221> NAME/KEY: VARIANT
<222> LOCATION: (8)..(8)
<223> OTHER INFORMATION: Xaa can be selected from: Ile, Ala, Leu, Met or
      Val
<220> FEATURE:
<221> NAME/KEY: VARIANT
<222> LOCATION: (9)..(9)
<223> OTHER INFORMATION: Xaa can be selected from: Ile, Leu, Met or Val
<220> FEATURE:
<221> NAME/KEY: VARIANT
<222> LOCATION: (10)..(10)
<223> OTHER INFORMATION: Xaa can be selected from: Tyr or Ser
<220> FEATURE:
<221> NAME/KEY: VARIANT
<222> LOCATION: (11)..(11)
<223> OTHER INFORMATION: Xaa can be selected from: Lys, Ala or Arg
<220> FEATURE:
<221> NAME/KEY: VARIANT
<222> LOCATION: (12)..(12)
<223> OTHER INFORMATION: Xaa can be selected from: Asn or Gln

<400> SEQUENCE: 10

Gly Ser Glu Thr Xaa Xaa Xaa Xaa Xaa Xaa Xaa Xaa
1               5                   10

<210> SEQ ID NO 11
<211> LENGTH: 4
<212> TYPE: PRT
<213> ORGANISM: Artificial Sequence
<220> FEATURE:
<223> OTHER INFORMATION: Peptide J

<400> SEQUENCE: 11

Gly Ser Glu Thr
1
```

```
<210> SEQ ID NO 12
<211> LENGTH: 8
<212> TYPE: PRT
<213> ORGANISM: Artificial Sequence
<220> FEATURE:
<223> OTHER INFORMATION: Reversed sequence of SEQ ID NO: 1

<400> SEQUENCE: 12

Asn Lys Thr Ile Ile Thr Lys Trp
1               5

<210> SEQ ID NO 13
<211> LENGTH: 12
<212> TYPE: PRT
<213> ORGANISM: Artificial Sequence
<220> FEATURE:
<223> OTHER INFORMATION: Reverse sequence of SEQ ID NO: 3

<400> SEQUENCE: 13

Asn Lys Thr Ile Ile Thr Lys Trp Thr Glu Ser Gly
1               5                   10

<210> SEQ ID NO 14
<211> LENGTH: 8
<212> TYPE: PRT
<213> ORGANISM: Artificial Sequence
<220> FEATURE:
<223> OTHER INFORMATION: IL13Ra2Nter

<400> SEQUENCE: 14

Phe Glu Ile Val Asp Pro Gly Tyr
1               5

<210> SEQ ID NO 15
<211> LENGTH: 8
<212> TYPE: PRT
<213> ORGANISM: Artificial Sequence
<220> FEATURE:
<223> OTHER INFORMATION: IL13Ra2Cter

<400> SEQUENCE: 15

Trp Ser Ile Pro Leu Gly Pro Ile
1               5

<210> SEQ ID NO 16
<211> LENGTH: 8
<212> TYPE: PRT
<213> ORGANISM: Artificial Sequence
<220> FEATURE:
<223> OTHER INFORMATION: IL13Ra2D1S-1A

<400> SEQUENCE: 16

Trp Ala Thr Ile Ile Thr Lys Asn
1               5

<210> SEQ ID NO 17
<211> LENGTH: 8
<212> TYPE: PRT
<213> ORGANISM: Artificial Sequence
<220> FEATURE:
<223> OTHER INFORMATION: IL13Ra2D1S-2A

<400> SEQUENCE: 17

Trp Lys Ala Ile Ile Thr Lys Asn
1               5
```

```
<210> SEQ ID NO 18
<211> LENGTH: 8
<212> TYPE: PRT
<213> ORGANISM: Artificial Sequence
<220> FEATURE:
<223> OTHER INFORMATION: IL13Ra2D1S-3A

<400> SEQUENCE: 18

Trp Lys Thr Ala Ile Thr Lys Asn
1               5

<210> SEQ ID NO 19
<211> LENGTH: 8
<212> TYPE: PRT
<213> ORGANISM: Artificial Sequence
<220> FEATURE:
<223> OTHER INFORMATION: IL13Ra2D1S-4A

<400> SEQUENCE: 19

Trp Lys Thr Ile Ala Thr Lys Asn
1               5

<210> SEQ ID NO 20
<211> LENGTH: 8
<212> TYPE: PRT
<213> ORGANISM: Artificial Sequence
<220> FEATURE:
<223> OTHER INFORMATION: IL13Ra2D1S-5A

<400> SEQUENCE: 20

Trp Lys Thr Ile Ile Ala Lys Asn
1               5

<210> SEQ ID NO 21
<211> LENGTH: 8
<212> TYPE: PRT
<213> ORGANISM: Artificial Sequence
<220> FEATURE:
<223> OTHER INFORMATION: IL13Ra2D1S-6A

<400> SEQUENCE: 21

Trp Lys Thr Ile Ile Thr Ala Asn
1               5

<210> SEQ ID NO 22
<211> LENGTH: 6
<212> TYPE: PRT
<213> ORGANISM: Artificial Sequence
<220> FEATURE:
<223> OTHER INFORMATION: Palindromic KTIITK residues

<400> SEQUENCE: 22

Lys Thr Ile Ile Thr Lys
1               5
```

IL13Rα2 PEPTIDE AND ITS USES

CROSS-REFERENCE TO RELATED APPLICATIONS AND PRIORITY

This patent application claims priority from PCT Patent Application No. PCT/EP2018/080193 filed Nov. 5, 2018, which claims priority from European Patent Application No. 17382737.9 filed Nov. 3, 2017. Each of these patent applications are herein incorporated by reference in its/their entirety.

FIELD OF THE INVENTION

The invention relates to the field of peptides and their therapeutic uses.

BACKGROUND OF THE INVENTION

Recent studies have identified a pro-metastatic role for human interleukin 13 (IL-13) in colorectal cancer mediated through the interleukin 13 receptor α2 (IL13Rα2). The binding of IL-13 to IL13Rα2 triggers different cellular pathways to promote migration, invasion and survival of the metastatic cells. In addition, IL13Rα2 is overexpressed in a variety of human tumor types such as glioblastoma, renal cell carcinoma, pancreatic, melanoma, head and neck, mesothelioma and ovarian, where it has been proposed as biomarker and potential therapeutic target. Multiple evidences suggest that IL-13 is the primary inducer of IL13Rα2. IL13Rα2 is quite different from the classical IL13Rα1 receptor, mainly expressed in immune cells, and might be present in two forms: a membrane signaling receptor and a soluble form with no signaling activity, which has been called the decoy receptor. Before recognizing its signaling capacity, the strong binding affinity of IL-13 to IL13Rα2 was interpreted as a way to sequester IL-13 and provoke its down-regulation. However, this interpretation does not explain IL-13 effects in pathologic conditions or IL13Rα2 overexpression in cancer. IL-13 signaling through IL13Rα2 in metastatic colorectal cancer cells was associated to the scaffold protein FAM120A, which activates FAK (focal adhesion kinase) and the PI3K (phosphoinositide 3-kinase) pathway and indirectly Src (proto-oncogene tyrosine kinase Src). Moreover, IL13Rα2 was associated also to multiple traffic proteins, which might explain its intracellular presence.

Targeting of IL-4 and IL-13 receptors for cancer therapy has been the subject of numerous studies and different strategies, including immunotoxins, DNA vaccines and specific monoclonal antibodies. Some trials involved the use of IL-13 immunotoxin, containing a truncated version of *Pseudomonas* exotoxin, which was highly cytotoxic to renal cancer cells and other human solid tumors (Puri R K et al., Blood 1996; 87:4333-9). Indeed, IL-13 immunotoxin has been used in a Phase III clinical trial with glioblastoma patients, showing small but significant effects on survival, Neuro Oncol 2010; 12:871-81). The problem of this strategy is the relative lack of specificity, as the IL-13 sequence also binds the low affinity receptor IL13Rα1, which is abundantly expressed in many normal tissues. In contrast normal tissues do not express IL13Rα2, with the exception of the testis. Another strategy made use of a high affinity antibody to IL13Rα2 that caused a modest increase in the survival of mice intracranially implanted with a human glioma xenograft (Balyasnikova I V et al., J Biol Chem 2012; 287:30215-27). Although promising, these alternatives have not delivered yet a substantial improvement in glioblastoma survival and no trials have been developed for metastatic colorectal cancer.

Therefore, there is a need for improved strategies for treating tumors and other diseases where IL13Rα2 is expressed, like glioblastoma and metastatic colorectal cancer.

BRIEF DESCRIPTION OF THE INVENTION

The authors of the present invention have surprisingly found that a 12-amino-acid-long peptide containing an 8 residues conserved sequence from the IL13Rα2 binding site was effective as therapeutic agent in metastatic colorectal cancer (FIG. 1C, 2A). The blocking peptide inhibited the different signaling pathways of IL-13 mediated through IL13Rα2 (FIG. 4) and significantly increased the mice survival by suppressing metastatic colonization (FIG. 6). In addition, the inventors demonstrated the superior effects of the D-enantio version of the peptide (FIG. 6).

Without being bound by any theory, it is thought that blocking the IL-13 signaling mediated through IL13Rα2 might increase the survival of patients through different mechanisms.

Thus, in a first aspect, the invention relates to a peptide comprising the amino acid sequence $X_1X_2X_3X_4X_5X_6X_7X_8$ (SEQ ID NO: 2) or its reversed sequence wherein
 $X_1$ is W, F or Y,
 $X_2$ is K or R,
 $X_3$ is T or S,
 $X_4$ is I, A, L, M or V,
 $X_5$ is I, L, M or V,
 $X_6$ is T or S,
 $X_7$ is K, A or R and
 $X_8$ is N or Q,
wherein said peptide is capable of inhibiting IL13/IL13Rα2 signalling.

In another aspect the invention relates to a fusion protein comprising the peptide of the invention and at least a heterologous polypeptide.

In another aspect the invention relates to a nanoparticle comprising the peptide or the fusion protein of the invention.

In another aspect the invention relates to a virus-like particle comprising the peptide or the fusion protein of the invention.

In another aspect the invention relates to a pharmaceutical composition comprising a therapeutically effective amount of the peptide, fusion protein, nanoparticle or virus-like particle of the invention, and a pharmaceutically acceptable excipient.

In another aspect the invention relates to the peptide, fusion protein, nanoparticle, virus-like particle according, or pharmaceutical composition of the invention for use in medicine.

In another aspect the invention relates to a peptide, fusion protein, nanoparticle, virus-like particle, or pharmaceutical composition of the invention for use in the treatment of a cancer, characterized by having increased expression of interleukin 13 receptor α2 (IL13R α2) compared to a reference value.

In another aspect the invention relates to a peptide, fusion protein, nanoparticle, virus-like particle, or pharmaceutical composition of the invention for use in the prevention of metastatic progression in a patient suffering from a cancer characterized by having increased expression of interleukin 13 receptor α2 (IL13R α2) compared to a reference value.

In another aspect the invention relates to a peptide, fusion protein, nanoparticle, virus-like particle, or pharmaceutical composition of the invention for use in the treatment of asthma, atopic dermatitis or fibrosis.

DETAILED DESCRIPTION OF THE INVENTION

Peptide of the Invention

Figure 1:
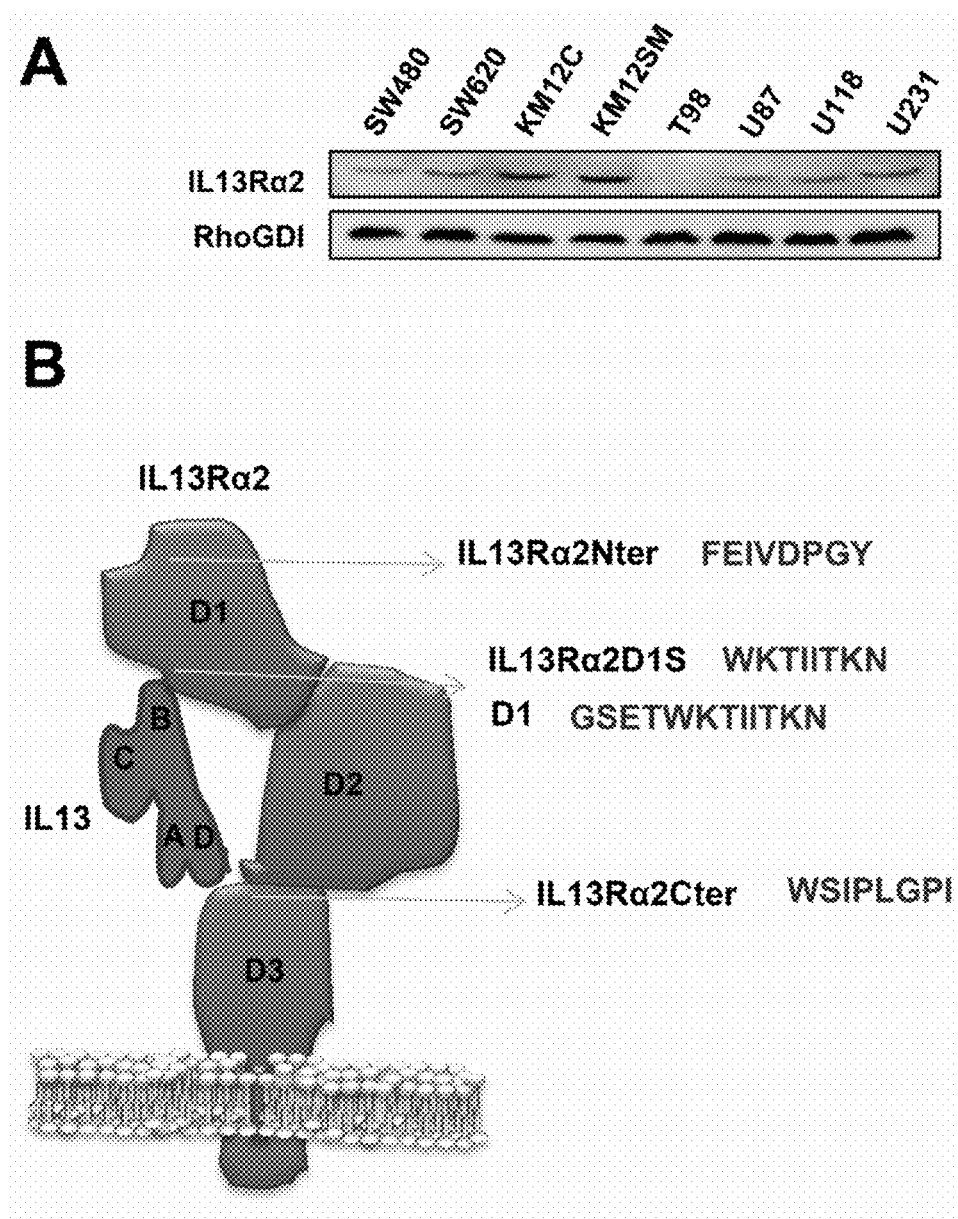
FIG. 1. Development of peptides derived from IL13Rα2 able to inhibit IL13 binding to its receptors. (A) Western blot analysis of IL13Rα2 expression in the indicated cell lines of colon cancer and glioblastoma. (B) Schematic representation of IL13Rα2, showing the regions of IL13 binding and the domains where the sequences for constructing the different peptides were extracted. IL13Rα2Nter SEQ ID NO: 14, IL13Rα2D1S SEQ ID NO: 1, D1 SEQ ID NO: 3, IL13Rα2Cter SEQ ID NO: 15. (C) KM12SM cells were treated with IL13 (20 ng/mL) and the indicated concentrations of D1 peptide and subjected to adhesion assays to Matrigel. Cell adhesion was significantly enhanced by IL13 (***, p<0.001). The presence of D1 peptide at the indicated concentration inhibited IL13-stimulated cell adhesion (◊◊, p<0.01; ◊◊◊, p<0.001).
Figure 1:
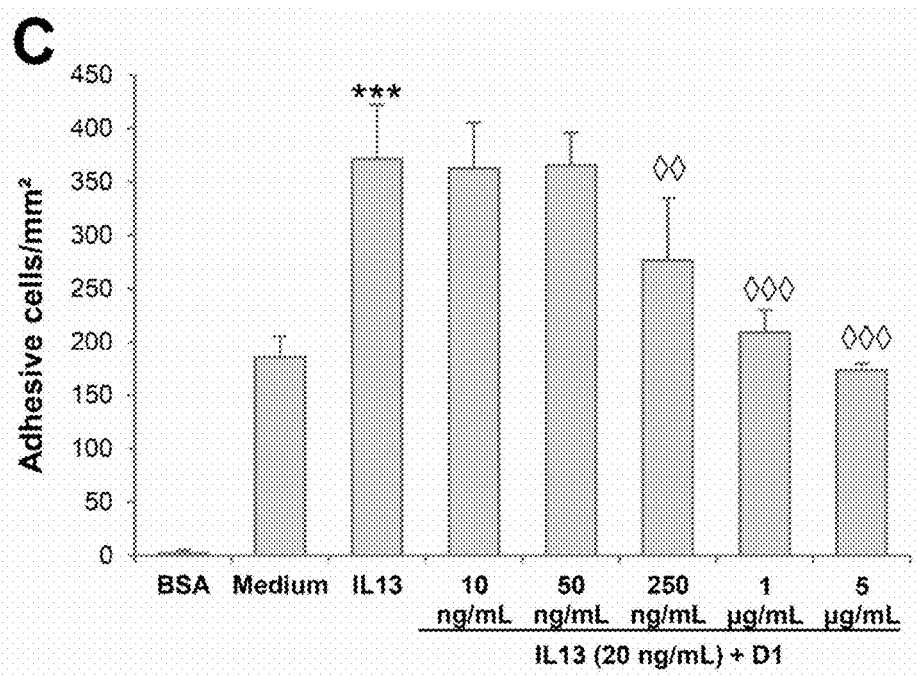

In a first aspect, the invention relates to a peptide, hereinafter peptide of the invention, comprising the amino acid sequence $X_1X_2X_3X_4X_5X_6X_7X_8$ (SEQ ID NO: 2) or its reversed sequence, wherein $X_1$ is W, F or Y,
$X_2$ is K or R,
$X_3$ is T or S
$X_4$ is I, A, L, M or V,
$X_5$ is L, M or V,
$X_6$ is T or S,
$X_7$ is K, A or R and
$X_8$ is N or Q, wherein said variant is capable of inhibiting IL13/IL13Rα2 signalling.

The term "peptide" or "polypeptide", as used herein, generally refers to a linear chain of around 2 to 50 amino acid residues joined together with peptide bonds. It will be understood that the terms "peptide bond", "peptide", "polypeptide" and protein are known to the person skilled in the art. From here on, "peptide" and "polypeptide" will be used indistinctly.

As used herein, an "amino acid residue" refers to any naturally occurring amino acid, any amino acid derivative or any amino acid mimic known in the art. The term "amino acid residue" encompasses both L- and D-amino acid residues.

In a particular embodiment, the peptide of the invention does not comprise the full-length sequence of the IL13Rα2, in particular, the full-length sequence of the human IL13Rα2 protein (SEQ ID NO: 9).

The term "interleukin-13 receptor subunit alpha-2" or "IL13Rα2", as used herein, refers to a protein that binds IL-13 with high affinity. In humans it is encoded by the gene IL13RA2. The IL13Rα2 can be of any origin, for example human, bovine, murine, equine, canine, etc. In a particular embodiment, the IL13Rα2 is the human protein with the Uniprot accession number Q14627 (entry version 170, 27 Sep. 2017; sequence version 1, 1 Nov. 1996).

In a particular embodiment, the peptide of the invention consist of less than 50, less than 40, less than 30, less than 20 or less than 10 amino acid residues.

In a particular embodiment, the peptide of the invention is between 8 and 50 amino acids in length, preferably between 8 and 40, more preferably between 8 and 30, even more preferably between 8 and 20.

In a particular embodiment, the peptide of the invention is 8 amino acids in length. In a more particular embodiment, the peptide of the invention is 8 amino acids in length and has the amino acid sequence WKTIITKN (SEQ ID NO: 1) or its reverse sequence.

In a particular embodiment, the peptide of the invention comprises the amino acid sequence WRTIITKN (SEQ ID NO: 5).

In a particular embodiment, the peptide of the invention comprises the amino acid sequence WKTIITRN (SEQ ID NO: 6).

In a particular embodiment, the peptide of the invention comprises the amino acid sequence WKTVITKN (SEQ ID NO: 7).

In a particular embodiment, the peptide of the invention comprises the amino acid sequence WKTIVTKN (SEQ ID NO: 8).

In a particular embodiment, the peptide of the invention comprises the amino acid sequence GSETWKTIITKN (SEQ ID NO: 3). In a more particular embodiment, the peptide of the invention comprises the reverse sequence of GSETWKTIITKN (SEQ ID NO: 3).

In a particular embodiment, the peptide of the invention is 12 amino acids in length. In a more particular embodiment, the peptide of the invention is 12 amino acids in length and has the amino acid sequence GSETWKTIITKN (SEQ ID NO:3) or its reversed sequence.

In a particular embodiment, the peptide of the invention comprises the reversed sequence of SEQ ID NO: 1. The term "reversed sequence", as used herein, refers to the amino acid sequence of a peptide read from its C-terminus to its N-terminus. As the skilled person will know, the reversed sequence of SEQ ID NO: 1 is NKTIITKW (SEQ ID NO: 12). As the skilled person will know, the reversed sequence of SEQ ID NO: 3 is NKTIITKWTESG (SEQ ID NO: 13).

In a particular embodiment, the peptide of the invention comprises a sequence which is a variant the of amino acid sequence of SEQ ID NO: 1 that has at least 50%, at least 60%, at least 70%, at least 75%, at least 80%, at least 85%, at least 90%, at least 91%, at least 92%, at least 93%, at least 94%, at least 95%, at least 96%, at least 97%, at least 98% or at least 99% sequence identity with SEQ ID NO: 1. The degree of identity between the variants and the SEQ ID NO: 1 is determined by using algorithms and computer methods which are widely known by the persons skilled in the art. The identity between two amino acid sequences is preferably determined by using the BLASTP algorithm [BLAST Manual, Altschul, S., et al., NCBI NLM NIH Bethesda, Md. 20894, Altschul, S., et al., J Mol Biol, 215: 403-410 (1990)]. In a preferred embodiment, the sequence identity is determined throughout the whole length of the sequence of SEQ ID NO: 1 or through the whole length of the variant or both.

In a particular embodiment, $X_4$ is I or A. In a more particular embodiment, $X_4$ is A.

In another particular embodiment, $X_7$ is K or A. in a more particular embodiment, $X_7$ is A.

In another particular embodiment, $X_4$ and $X_7$ are both A.

In a particular embodiment, the variant has the amino acid sequence WKTAITAN (SEQ ID NO: 4).

According to the present invention, the variant of the amino acid sequence of SEQ ID NO: 1 is capable of inhibiting IL13/IL13Rα2 signaling, that is, the signaling of the receptor IL13Rα2 mediated by IL13. The ability of a peptide to inhibit IL13/IL13Rα2 signaling can be determined by measuring the ability of the peptide to block the activation of IL-13 targets mediated by IL13Rα2, namely, FAK (focal adhesion kinase), ERK1/2 (extracellular signal-regulated kinase ½), Src (proto-oncogene tyrosine kinase Src) and AKT (RAC-alpha serine/threonine-protein kinase). The activation of FAK, ERK1/2, Src and AKT by IL-13 can be determined by any suitable method known by the skilled person, for example, by determining the amount of the corresponding phosphorylated forms phospho-FAK, phospho-ERK1/2, phospho-Src and phospho-AKT after IL-13 treatment, as described in the examples of the present document. In a particular embodiment, it is considered that a peptide is capable of inhibiting IL13/IL13Rα2 signaling if it reduces the IL-13 induced phosphorylation of any of FAK, ERK1/2, Src and AKT in at least a 5%, at least a 10%, at least a 20%, at least a 30%, at least a 40%, at least a 50%, at least a 60%, at least a 70%, at least a 80%, at least a 90% or a 100%.

In a particular embodiment, the peptide of the invention comprises at least one D-amino acid. The term "D-amino acid", as used herein, refers to the D-enantiomer of an amino acid, which is the mirror image of the L-amino acid.

In a particular embodiment, the peptide of the invention comprises 2, 3, 4, 5, 6, 7, 8 or more D-amino acids.

In a particular embodiment, the peptide of the invention consists entirely of D-amino acids, that is, it is an all-D-enantiomer. As the skilled person knows, glycine is the only amino acid that has no enantiomer, so in this particular embodiment it is not excluded that the peptide comprises glycine.

In another particular embodiment, the peptide of the invention comprises the all-D-enantiomer of the sequence $X_1X_2X_3X_4X_5X_6X_7X_8$ (SEQ ID NO: 2).

In a particular embodiment, the peptide of the invention comprises the all-D-enantiomer of the sequence WKTIITKN (SEQ ID NO: 1) or the reverse variant thereof.

In a particular embodiment, the peptide of the invention comprises the all-D-enantiomer of the sequence GSETWKTIITKN (SEQ ID NO: 3) or the reverse variant thereof.

In a particular embodiment, the peptide of the invention comprises the all-D-enantiomer of the sequence WKTAITAN (SEQ ID NO: 4) or the reverse variant thereof The peptide of the invention can be obtained by any suitable method known in the art, for example, by chemical synthesis or by recombinant protein techniques.

Fusion Protein, Nanoparticle and Virus-Like Particle of the Invention

In another aspect, the invention relates to a fusion protein comprising the peptide of the invention and least a heterologous polypeptide.

The peptide of the invention has been previously defined. All the particular and preferred embodiments of the peptide of the invention are fully applicable to the fusion protein of the invention.

The term "fusion protein", as used herein, refers to a single polypeptide chain artificially designed which comprises two or more sequences from different origins, natural and/or artificial. The fusion protein, per definition, is never found in nature as such.

The term "heterologous polypeptide", as used herein, means that the polypeptide is not naturally found fused to the peptide of the invention.

In a particular embodiment, the heterologous polypeptide is a peptide that is capable of crossing the blood-brain barrier. Conjugation of the peptide of the invention to this type of peptide will facilitate the peptide to cross the blood-brain barrier and is especially useful for delivering the peptide in the central nervous system by systemic administration. Peptides capable of crossing the blood-brain barrier are known in the art. For example, WO200979790 a series of peptides collectively known as Angiopeps which are capable of crossing the blood-brain barrier by receptor-mediated transcytosis using the low-density lipoprotein receptor-related protein-1 (LRP-1) and which allows the delivery to the CNS of systemically administered conjugates comprising said peptides. WO2011087804 describes a peptide derived from rabies virus glycoprotein G, which allows the conjugate comprising said peptide to cross the blood-brain barrier. Padres et al., Angewandte Chemie 2015, 54: 3967-72 describes a 12 amino acid-peptide derived from the human transferrin peptide which is capable of overcome the blood-brain barrier.

The fusion protein of the invention can be obtained by any suitable technique that allows obtaining two peptides (the peptide of the invention and the heterologous polypeptide) in a single polynucleotide chain. Said techniques include recombinant techniques, where a gene construct encoding the fusion protein is introduced in to a vector suitable for expression in a suitable expression system, and protein ligation techniques involving the formation of a peptide bond between two polypeptides, like native chemical ligation or expressed protein ligation.

In another aspect, the invention relates to a nanoparticle comprising the peptide or the fusion protein of the invention.

The peptide and the fusion protein have been previously defined. All the particular and preferred embodiments of the peptide and the fusion protein of the invention are fully applicable to the nanoparticle of the invention.

The term "nanoparticle", as used herein, refers to any material having dimensions in the 1-1,000 nm range. In some embodiments, nanoparticles have dimensions in the 2-200 nm range, preferably in the 2-150 nm range, and even more preferably in the 2-100 nm range.

The nanoparticles may contribute to preserve the integrity of the peptide or of the fusion protein in the biological fluids until it reaches the target organ. Moreover, in the case of fusion comprising an antitumor polypeptide, encapsulation of the composition may decrease secondary effects caused by the antitumor agent. Lastly, nanoparticles can also be modified so as to include moieties which allow the targeting of the nanoparticle to an organ of interest.

Suitable nanoparticles that can be used in the context of the present invention include such nanoscale materials as a lipid-based nanoparticle, a superparamagnetic nanoparticle, a nanoshell, a semiconductor nanocrystal, a quantum dot, a polymer-based nanoparticle, a silicon-based nanoparticle, a silica-based nanoparticle, a metal-based nanoparticle, a fullerene and a nanotube.

Targeted delivery can be achieved by the addition of ligands without compromising the ability of nanoparticles to deliver their peptide payloads. It is contemplated that this will enable delivery to specific cells, tissues and organs. The targeting specificity of the ligand-based delivery systems is based on the distribution of the ligand receptors on different cell types. The targeting ligand may either be non-covalently or covalently associated with a nanoparticle, and can be conjugated to the nanoparticles by a variety of methods as discussed herein.

Examples of proteins or peptides that can be used to target nanoparticles include transferin, lactoferrin, TGF-β, nerve growth factor, albumin, HIV Tat peptide, RGD peptide, and insulin, as well as others.

It will be understood that the formulation of the product of the invention in a nanoparticle is not intended or is not solely intended for facilitating the access of the product to the interior of the cell but to protect the product from degradation and/or for facilitating targeting of the nanoparticle to the organ of interest.

In another aspect, the invention refers to a virus-like particle comprising the peptide or the fusion protein of the invention.

The peptide and fusion protein of the invention have been previously defined. All the particular and preferred embodiments of the peptide and fusion protein of the invention are fully applicable to the nucleic acid and gene construct of the invention.

The term "virus-like particle", also referred to as "VLP", relates to non-infectious particles resembling viruses that do not contain any viral genetic material. VLPs are the result of the expression of viral structural proteins, such as capsid proteins, and their self-assembly.

In a particular embodiment, the VLP can comprise, or alternatively consist of, structural proteins of Parvovirus, Rotavirus; structural proteins of Norwalk virus; structural proteins of Alphavirus; structural proteins of Foot and Mouth Disease virus; structural proteins of measles virus, structural proteins of Sindbis virus, structural proteins of Retrovirus structural proteins of Hepatitis B virus (e.g., a HBcAg); structural proteins of Tobacco mosaic virus; structural proteins of Flock House Virus; structural proteins of human Papillomavirus; structural proteins of Polyoma virus; structural proteins of bacteriophages, structural proteins of RNA phages.

In a particular embodiment, the peptide or fusion protein of the invention is coupled or attached to the capsid of the virus-like particle. The attachment of the peptide or fusion protein to the capsid can be by a covalent or non-covalent link.

Nucleic Acid, Gene Construct, Vector and Cell of the Invention

In another aspect, the invention relates to a nucleic acid encoding the peptide or the fusion protein of the invention and to a gene construct comprising said nucleic acid.

The terms peptide and fusion protein of the invention have been previously defined. All the particular and preferred embodiments of the peptide and fusion protein of the invention are fully applicable to the nucleic acid and gene construct of the invention.

The terms "polynucleotide", "nucleic acid" and "nucleic acid molecule" are used interchangeably to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes, for example, single-stranded, double-stranded and triple helical molecules, a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. In addition to a native nucleic acid molecule, a nucleic acid molecule of the present invention may also comprise modified nucleic acid molecules. As used herein, mRNA refers to an RNA that can be translated in a cell.

In preferred embodiment, the polynucleotide of the invention is an mRNA. mRNA can be chemically synthesized, can be obtained by means of in vitro transcription or can be synthesized in vivo in the target cell. The nucleotide sequences that form the nucleic acid encoding the conjugate or fusion protein of the invention are in the same correct reading frame for expression thereof.

The term "gene construct", as used herein, refers to the nucleic acid of the invention together with regions suitable for regulating the expression of said nucleic acid, including promoters, transcription terminators, untranslated 5' and 3' regions, polyadenylation signals and similars.

In another aspect, the invention relates to a vector comprising a polynucleotide of the invention.

The term "vector", as used herein, refers to a nucleic acid sequence comprising the necessary sequences so that after transcribing and translating said sequences in a cell a polypeptide encoded by the nucleic acid of the invention is generated. Said sequence is operably linked to additional segments that provide for its autonomous replication in a host cell of interest. Preferably, the vector is an expression vector, which is defined as a vector which, in addition to the regions of the autonomous replication in a host cell, contains regions operably linked to the nucleic acid of the invention and which are capable of enhancing the expression of the products of the nucleic acid according to the invention. The vectors of the invention can be obtained by means of techniques widely known in the art.

Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

The vector of the invention may be used to transform, transfect or infect cells that can be transformed, transfected or infected by said vector. Said cells may be prokaryotic or eukaryotic.

The vector preferably comprises the nucleic acid of the invention operationally bound to sequences that regulate the expression of the nucleic acid of the invention. The regulatory sequences of use in the present invention may be nuclear promoters or, alternatively, enhancer sequences and/or other regulatory sequences that increase expression of the heterologous nucleic acid sequence. In principle, any promoter can be used in the present invention provided said promoter is compatible with the cells wherein the nucleic acid is to be expressed.

In another aspect, the invention relates to a cell comprising the peptide, fusion protein, nucleic acid, gene construct or vector of the invention.

The peptide, fusion protein, nucleic acid, gene construct and vector of the invention have been previously defined. All the particular and preferred embodiments of the peptide, fusion protein, nucleic acid, gene construct and vector of the invention are fully applicable to the nucleic acid and gene construct of the invention.

Cells suitable in the present invention include, but are not limited to, mammalian, plant, insect, fungal and bacterial cells.

Pharmaceutical Composition of the Invention

In another aspect, the invention relates to a pharmaceutical composition comprising a therapeutically effective amount of the peptide, fusion protein, nanoparticle, virus-like particle, nucleic acid, gene construct, vector, or cell of the invention, and a pharmaceutically acceptable excipient.

The peptide, fusion protein, nanoparticle, virus-like particle, nucleic acid, gene construct, vector, and cell of the invention have been previously defined. All the particular and preferred embodiments of the peptide, fusion protein, nanoparticle, virus-like particle, nucleic acid, gene construct, vector, and cell of the invention are fully applicable to the nucleic acid and gene construct of the invention.

As it is used in the present invention, the expression "pharmaceutical composition" relates to a formulation that has been adapted for administering a predetermined dose of one or several therapeutic useful agents to a cell, a group of cells, an organ, a tissue or an animal in which cell division is uncontrolled, such as cancer.

The expression "therapeutically effective amount", as used herein, is understood as an amount capable of providing a therapeutic effect, and which can be determined by the person skilled in the art by commonly used means. The amount of the peptide, fusion protein, nanoparticle, nucleic acid, gene construct, vector, virus or viral particle or cell of the invention that may be included in the pharmaceutical compositions according to the invention will vary depending upon the subject and the particular mode of administration. Those skilled in the art will appreciate that dosages may also be determined with guidance from Goodman and Goldman's The Pharmacological Basis of Therapeutics, Ninth Edition (1996), Appendix II, pp. 1707-1711 and from Goodman and Goldman's The Pharmacological Basis of Therapeutics, Tenth Edition (2001), Appendix II, pp. 475-493.

The appropriate dosage of the active principle or principles within the pharmaceutical composition will depend on the type of cancer to be treated, the severity and course of the disease, whether the composition is administered for preventive or therapeutic purposes, previous therapy, the patient's clinical history and response to the peptide or polypeptide, and the discretion of the attending physician. The amount of the peptide, fusion protein, nanoparticle, nucleic acid, gene construct, vector, virus or viral particle or cell of the invention is suitably administered to the patient at one time or over a series of treatments. Depending on the type and severity of the disease, an appropriate dosage level will generally be about 0.1 to about 10 mg/kg; more preferably about 0.5 to about 5 mg/kg, even more preferably about 0.75 to about 2.5 mg/kg, still more preferably about 1 mg/kg, which can be administered in single or multiple doses. The compounds may be administered on a regimen of 1 to several times per day or per two, three, four, five, six or seven days, preferably once each two days. The pharmaceutical composition may be administered during at least 1, 2, 3, 4, 5, 6, 7, 14, 21, 28 or more days, preferably during 14 days. The pharmaceutical composition may be preferably administered once each two days during 14 days.

The pharmaceutical compositions of the invention also contain one or several additional pharmaceutically acceptable excipients. "Pharmaceutically acceptable excipient" is understood a therapeutically inactive substance said to be used for incorporating the active ingredient and which is acceptable for the patient from a pharmacological/toxicological point of view and for the pharmaceutical chemist who manufactures it from a physical/chemical point of view with respect to the composition, formulation, stability, acceptation of the patient and bioavailability. The excipient or carrier also includes any substance that serves to improve the delivery and the effectiveness of the active principle within the pharmaceutical composition. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the fusion protein or of the compositions forming part of the pharmaceutical compositions. Examples of proper carriers are well known in the literature (see for example Remington's Pharmaceutical Sciences, 19th ed., Mack Publishing Company, Easton, Pa., 1995). Examples of carriers without limitation are a series of saccharide such as lactose, dextrose, sucrose, sorbitol, mannitol, xylitol, erythritol, and maltitol; a series of starch such as corn starch, wheat starch, rice starch, and potato starch; a series of cellulose such as cellulose, methyl cellulose, sodium carboxy methyl cellulose, and hydroxyl propylmethyl cellulose; and a series of filler such as gelatin and polyvinyl pyrrolidone. In some cases, a disintegrant such as cross-linked polyvinyl pyrrolidone, agar, alginic acid, or sodium alginate may be added.

The number and the nature of the pharmaceutically acceptable excipients depend on the desired dosage form. The pharmaceutically acceptable excipients are known by the person skilled in the art (Faulí y Trillo C. (1993) "Tratado de Farmacia Galénica", Luzán 5, S. A. Ediciones, Madrid). Said compositions can be prepared by means of the conventional methods known in the state of the art ("Remington: The Science and Practice of Pharmacy", 20$^{th}$ edition (2003) Genaro A. R., ed., Lippincott Williams & Wilkins, Philadelphia, U.S.).

The pharmaceutical compositions of the invention can be administered by any type of suitable route, such as by oral, nasal, ocular, topical, intradermic, intracranial or intravenous route. The preferred route of administration of said pharmaceutical compositions is the oral, nasal, ocular, topical, intracranial or intradermic route.

"Oral route" is understood as the pharmaceutical composition incorporated into the organism after deglutition.

"Nasal route" is understood as the administration of the pharmaceutical composition insufflated through the nose.

"Ocular route" is understood as the topical administration of the pharmaceutical composition by instillation directly to the eye.

"Topical route is understood as the application in the exterior of the body such as, without limitation, the skin, scalp and nails; and also the application to mucosae such as, without limitation, buccal, nasal or rectal mucosae.

"Intradermic route" is understood as the administration of the pharmaceutical composition by the injection into the dermis.

"Intracranial route" is understood as the administration of the pharmaceutical compositing within the skull.

"Intravenous route" is understood as the administration of the pharmaceutical composition by the injection into the blood flow.

Medical Uses of the Invention

In another aspect, the invention relates to the peptide, fusion protein, nanoparticle, virus-like particle, nucleic acid, gene construct, vector, cell or pharmaceutical composition of the invention for use in medicine.

Alternatively, the invention relates to the use of the peptide, fusion protein, nanoparticle, virus-like particle, nucleic acid, gene construct, vector, cell or pharmaceutical composition of the invention for the manufacture of a medicament.

Figure 2:
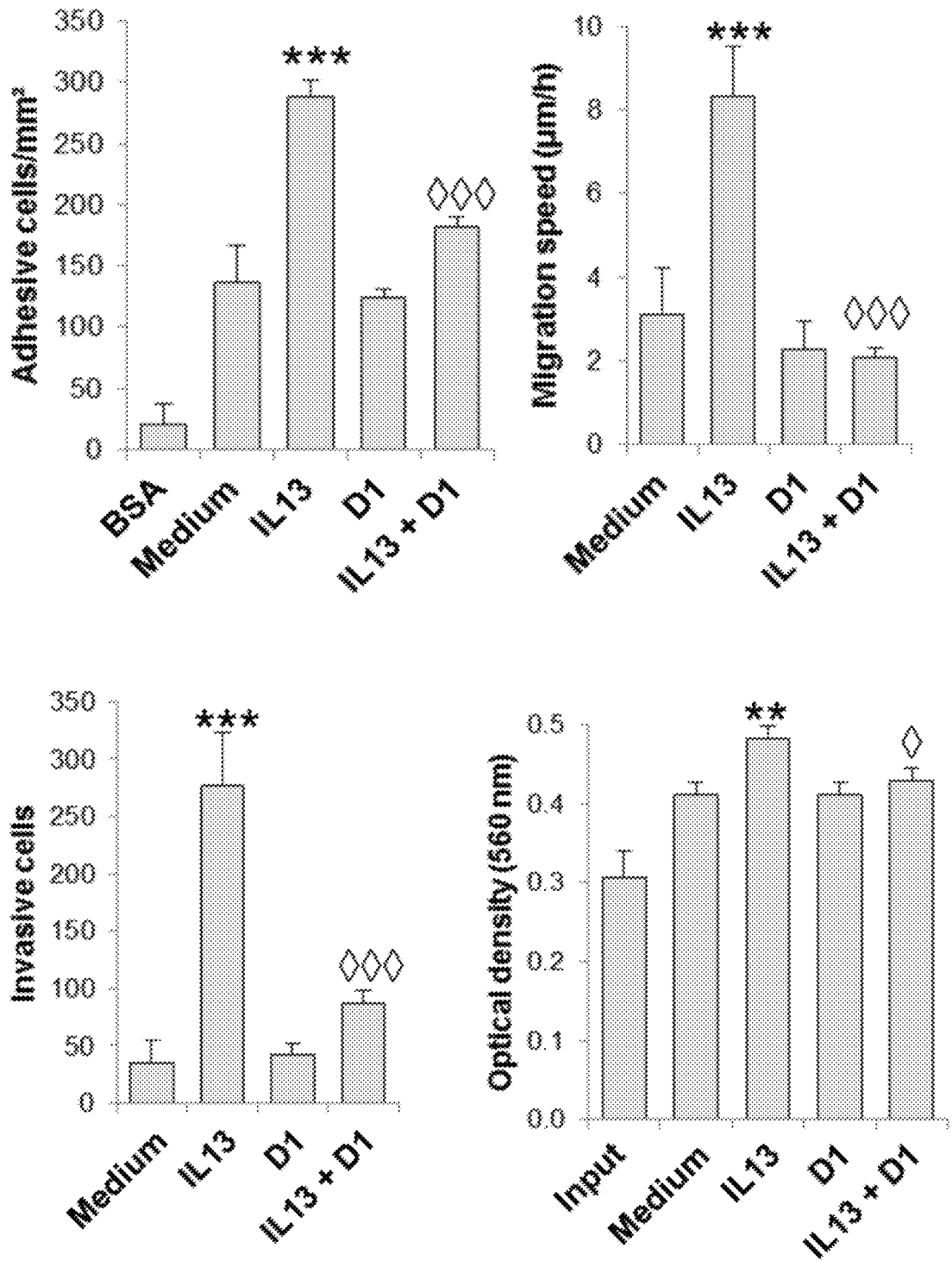
FIG. 2. D1 peptide inhibits cell migration, invasion and proliferation of colon cancer and glioblastoma cells. (A) KM12SM and SW620 colon cancer cells were subjected to cell adhesion assays to Matrigel, wound healing assays, cell invasion assays through Matrigel and MTT assays in the presence of IL13 and/or D1 peptide. (B) U87 and U118 glioblastoma cells were subjected to the same assays as in (A) in the presence of IL13 and/or D1 peptide. Number of adhesive cells, effective migration speed, number of invasive cells or number of viable cells was significantly enhanced by the presence of IL13 (*, p<0.05; , p<0.01; *, p<0.001). Such stimulations of cell adhesion, migration invasion and proliferation triggered by IL13 were inhibited by the presence of D1 peptide IL13 (◊, p<0.05; ◊◊◊, p<0.001).
Figure 2:
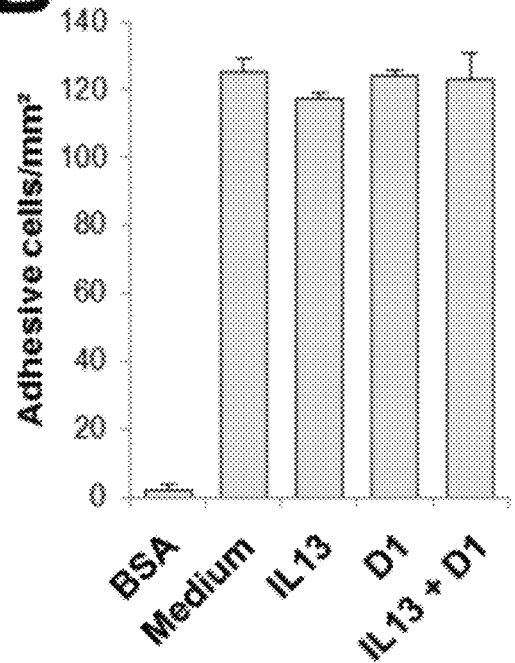
Figure 2:
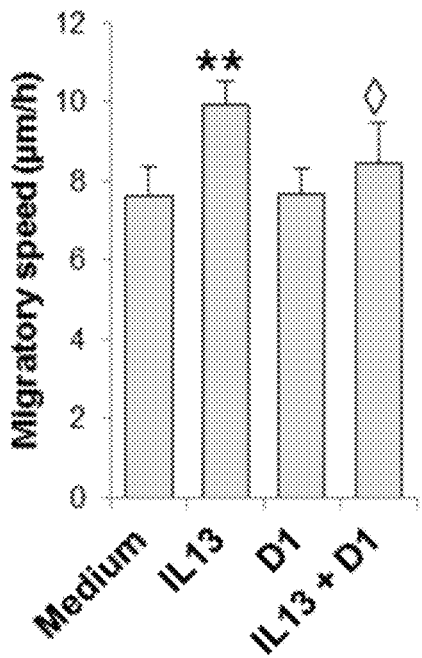
Figure 2:
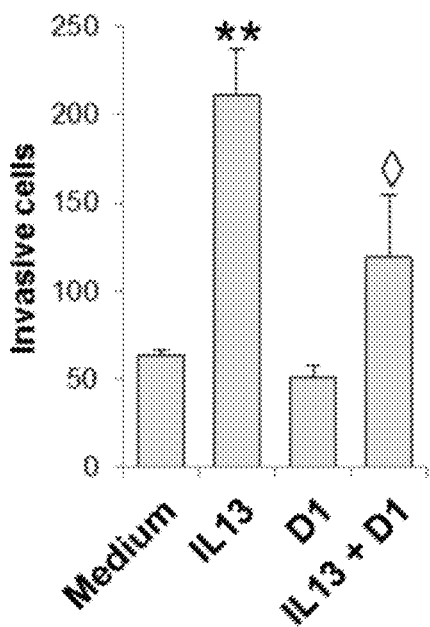
Figure 2:
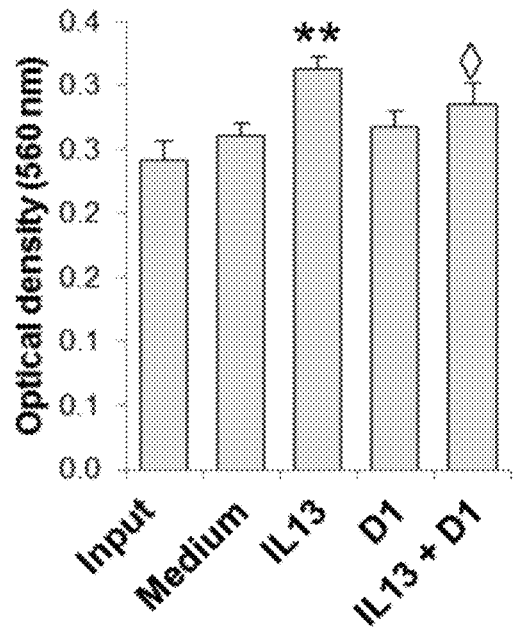
Figure 4:
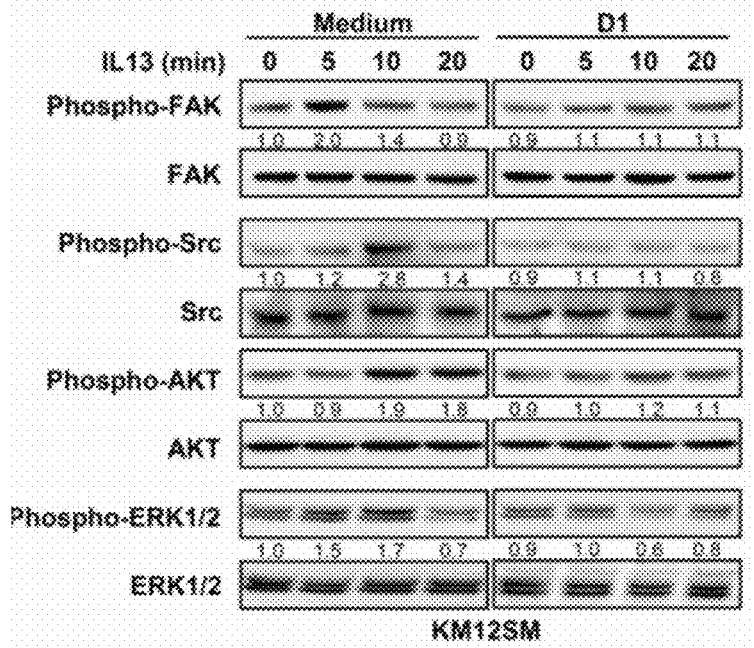
FIG. 4. D1 peptide inhibits IL-13 mediated cell signaling. KM12SM (A) or U87 (B) cells were detached, resuspended in serum-free DMEM in absence or presence of D1 peptide and treated with IL-13 for the indicated times. Cells were lysed, and the extracts were analyzed by Western blotting with antibodies against FAK, Src, ERK1/2, AKT and their phosphorylated forms. In both types of cancer cells, a clear inhibitors effect was observed for phospho-FAK, Src, ERK1/2 and AKT.
Figure 4:
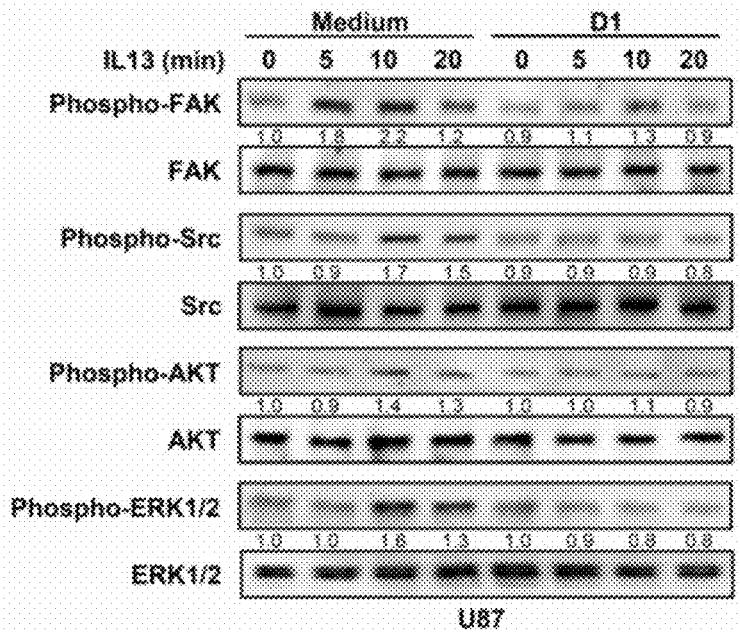

The authors of the present invention have shown that 12-amino-acid-long peptide containing an 8 residues conserved sequence from the IL13Rα2 binding site was effective as therapeutic agent in metastatic colorectal cancer (FIG. 1C, 2A) and glioblastoma (FIG. 1A) and that this peptide inhibits IL-13 mediated cell signaling in colorectal and glioblastoma cells (FIG. 4). Therefore, in another aspect, the invention relates to the peptide, fusion protein, nanoparticle, virus-like particle, nucleic acid, gene construct, vector, cell or pharmaceutical composition of the invention for use in the treatment of a cancer characterized by having increased expression of interleukin 13 receptor α2 (IL13Rα2) compared to a reference value.

Alternatively, the invention relates to the use of the peptide, fusion protein, nanoparticle, virus-like particle, nucleic acid, gene construct, vector, cell or pharmaceutical composition of the invention for the manufacture of a medicament for the treatment of a cancer characterized by having increased expression of interleukin 13 receptor α2 (IL13Rα2) compared to a reference value.

Alternatively, the invention relates to a method for treating a cancer characterized by having expression of interleukin 13 receptor α2 (IL13Rα2) comprising administering to a patient a therapeutically effective amount of the the peptide, fusion protein, nanoparticle, virus-like particle, nucleic acid, gene construct, vector, cell or pharmaceutical composition of the invention.

Figure 6:
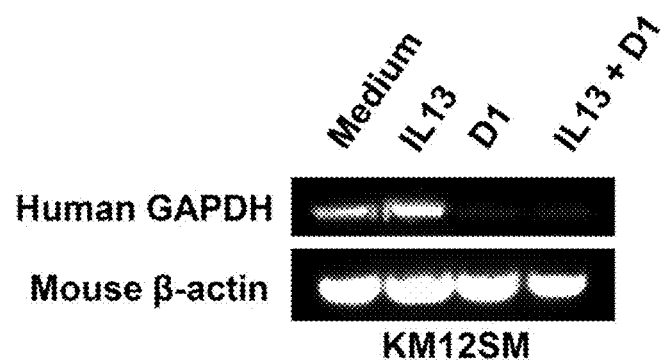
FIG. 6. D1 and D-D1 peptides increase the survival of mice inoculated with metastatic tumor cells and inhibits glioblastoma xenografts. (A) Liver homing experiment. Metastatic KM12SM cells were treated with the IL13 and/or D1 peptide and inoculated in spleen of nude mice. 48 h after inoculation RNA was isolated from liver, and subjected to RT-PCR to amplify human GAPDH, and mouse β-actin as loading control. (B) Kaplan-Meier survival assay of nude mice inoculated with KM12SM cells in the spleen in presence of the indicated peptides with or without additional treatment. For mice with peptide treatment, 48 h after inoculation and for 2 weeks, the indicated peptides were administered intravenously in seven doses. When signs of illness were detected, mice were euthanized. Survival was significantly enhanced after treatment with the indicated peptide (*, p<0.05; *, p<0.001). (C) $10^7$ U251 cells were inoculated subcutaneously into the flanks of mice. Eleven days after cell inoculation, when tumours reached a size of 100 mm$^3$, mice were treated with D-D1 peptide (3 μg/100 μL of PBS) subcutaneously or with saline solution in a total of 7 doses during 15 days. Tumours were measured every 2-3 days. p<0.01 vs control.
Figure 6:
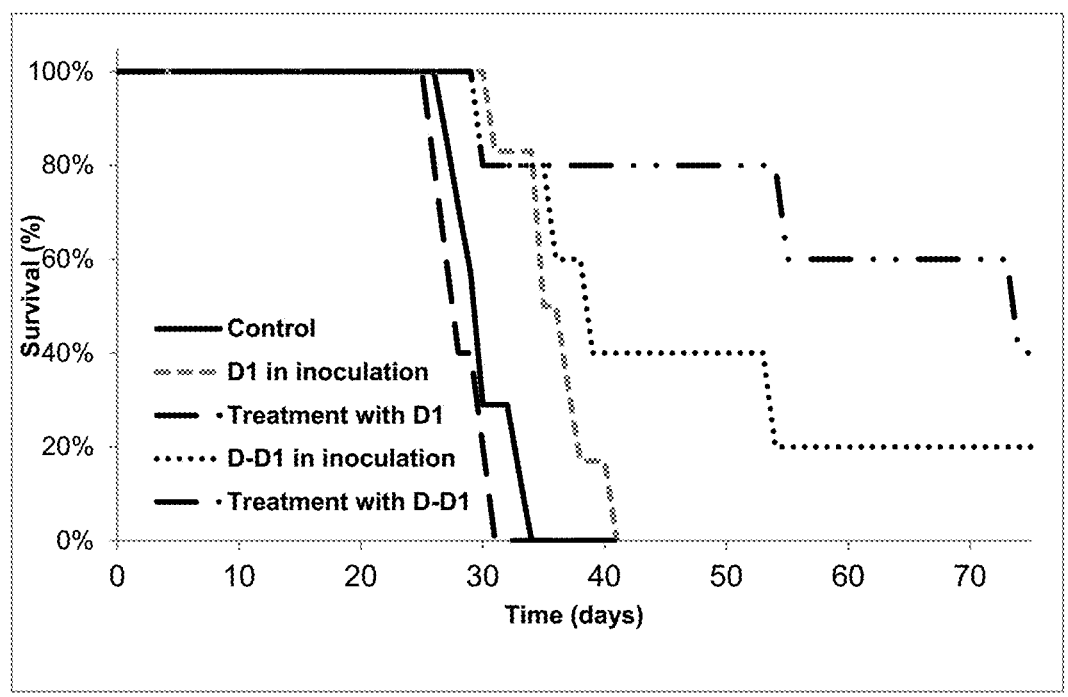
Figure 6:
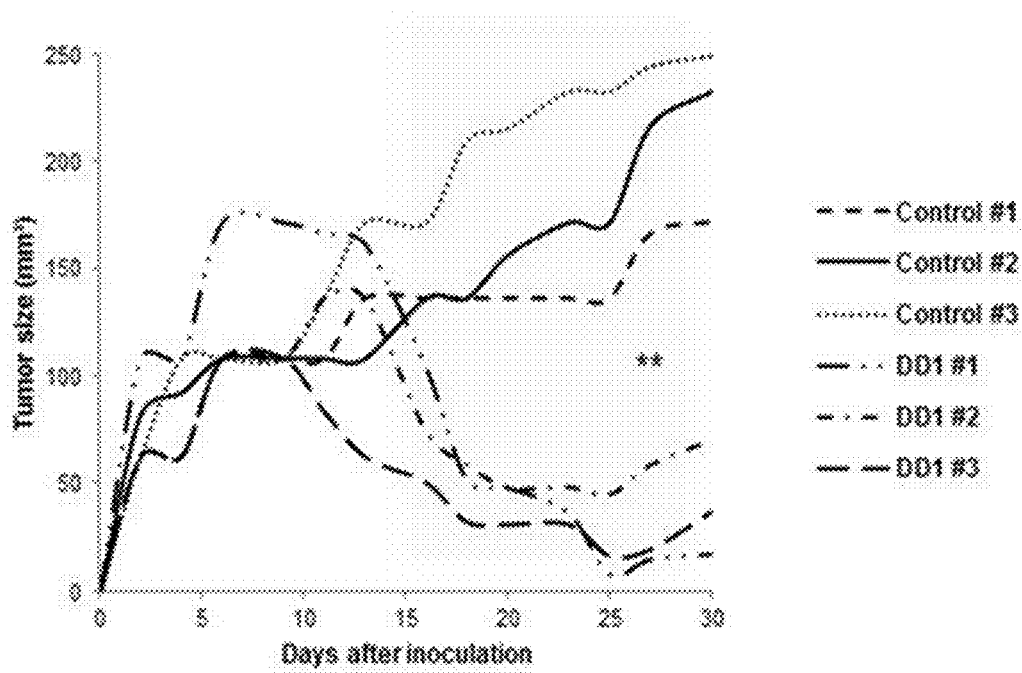

Additionally, the inventors have shown that the IL13Rα2 derived peptide inhibits the metastatic capacity of colorectal and glioblastoma cells in vitro (FIGS. 1 and 2) and of colorectal cells using in vivo models (FIG. 6A, B). Therefore, in another aspect, the invention relates to the peptide, fusion protein, nanoparticle, virus-like particle, nucleic acid, gene construct, vector, cell or pharmaceutical composition of the invention for use in the prevention of metastatic progression in a patient suffering from a cancer characterized by having increased expression of interleukin 13 receptor α2 (IL13Rα2) compared to a reference value.

Alternatively, the invention relates to the use of the peptide, fusion protein, nanoparticle, virus-like particle, nucleic acid, gene construct, vector, cell or pharmaceutical composition of the invention for the manufacture of a medicament for the prevention of metastatic progression in a patient suffering from a cancer characterized by having increased expression of interleukin 13 receptor α2 (IL13Rα2) compared to a reference value.

Alternatively, the invention relates to a method for preventing the metastatic progression of a cancer characterized by having increased expression of interleukin 13 receptor α2 (IL13Rα2) compared to a reference value, comprising administering to a patient a therapeutically effective amount of the the peptide, fusion protein, nanoparticle, virus-like particle, nucleic acid, gene construct, vector, cell or pharmaceutical composition of the invention.

Overexpression of IL13Rα2 has been reported in several diseases, including allergic asthma, atopic dermatitis and fibrosis (Mentink-Kane and Wynn, Immunol Rev 2004, 202: 191-202; Popovic et al, J Mol Biol 2017 429, 208-219; Gour and Wills-Karp, Cytokine 2015, 75: 68-78). Therefore, it another aspect, the invention relates to the peptide, fusion protein, nanoparticle, virus-like particle, nucleic acid, gene construct, vector, cell or pharmaceutical composition of the invention for use in the treatment of asthma, atopic dermatitis or fibrosis.

Alternatively, the invention relates to the use of the peptide, fusion protein, nanoparticle, virus-like particle, nucleic acid, gene construct, vector, cell or pharmaceutical composition of the invention for the manufacture of a medicament for the treatment of asthma, atopic dermatitis or fibrosis.

Alternatively, the invention relates to a method for treating asthma, atopic dermatitis or fibrosis comprising administering to a patient a therapeutically effective amount of the the peptide, fusion protein, nanoparticle, virus-like particle, nucleic acid, gene construct, vector, cell or pharmaceutical composition of the invention.

The peptide, fusion protein, nanoparticle, virus-like particle, nucleic acid, gene construct, vector, cell and pharmaceutical composition of the invention have been previously defined. All the particular and preferred embodiments of the peptide, fusion protein, nanoparticle, nucleic acid, gene construct, vector, cell and pharmaceutical composition of the invention are fully applicable to the nucleic acid and gene construct of the invention.

The term "treatment", as used herein, refers to any process, action, application, therapy, or the like, wherein a subject (or patient), including a human being, is provided medical aid with the object of improving the subject's condition, directly or indirectly, or slowing the progression of a condition or disorder in the subject, or ameliorating at least one symptom of the disease or disorder under treatment.

The term "prevention", as used herein, refers to the capacity of peptide, fusion protein, nucleic acid, nanoparticle, virus-like particle, gene construct, vector, cell and pharmaceutical composition of the invention, to prevent, minimize or hinder the metastatic progression of a cancer characterized by having increased expression of interleukin 13 receptor α2 (IL13Rα2) compared to a reference value.

The term "metastatic progression", as used herein, refers to the process through which a tumor spreads to body tissues different than the primary site of tumor origin. In a particular embodiment, the metastasis is selected from the group consisting of lung, liver and brain metastasis.

The term "patient" or "subject", as used herein, refers to any animal, preferably a mammal and includes, but is not limited to, domestic and farm animals, primates, and humans, for example, human beings, non-human primates, cows, horses, pigs, sheep, goats, dogs, cats, or rodents like rats and mice. In a preferred embodiment, the subject is a human being of any age or race. In a particular embodiment, the subject suffers from a cancer characterized by having increased expression of interleukin 13 receptor α2 (IL13Rα2) compared to a reference value.

The term "therapeutically effective amount" has been previously defined.

The term "cancer", as used herein, refers to a disease characterized by uncontrolled cell division (or by an increase of survival or apoptosis resistance) and by the ability of said cells to invade other neighboring tissues (invasion) and spread to other areas of the body where the cells are not normally located (metastasis) through the lymphatic and blood vessels, circulate through the bloodstream, and then invade normal tissues elsewhere in the body. Depending on whether or not they can spread by invasion and metastasis, tumors are classified as being either benign or malignant: benign tumors are tumors that cannot spread by invasion or metastasis, i.e., they only grow locally; whereas malignant tumors are tumors that are capable of spreading by invasion and metastasis. Biological processes known to be related to cancer include angiogenesis, immune cell infiltration, cell migration and metastasis. As used herein, the term cancer includes, but is not limited to, the following types of cancer: breast cancer; biliary tract cancer; bladder cancer; brain cancer including glioblastomas and medulloblastomas; cervical cancer; choriocarcinoma; colon cancer; endometrial cancer; esophageal cancer; gastric cancer; hematological neoplasms including acute lymphocytic and myelogenous leukemia; T-cell acute lymphoblastic leukemia/lymphoma; hairy cell leukemia; chronic myelogenous leukemia, multiple myeloma; AIDS-associated leukemias and adult T-cell leukemia/lymphoma; intraepithelial neoplasms including Bowen's disease and Paget's disease; liver cancer; lung cancer; lymphomas including Hodgkin's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer; rectal cancer; sarcomas including leiomyosarcoma, rhabdomyosarcoma, liposarcoma, fibrosarcoma, and osteosarcoma; skin cancer including melanoma, Merkel cell carcinoma, Kaposi's sarcoma, basal cell carcinoma, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma and Wilms tumor.

The term "cancer characterized by having increased expression of interleukin 13 receptor α2 (IL13Rα2) compared to a reference value", as used herein, refers to the fact that the cancer contains cells having increased expression levels of IL13Rα2 compared to a reference value. The term "expression levels", as used herein, refers to the level of the product of IL13Rα2 gene, that is, the levels of the messenger RNA or of the protein encoded by said gene. The presence of messenger RNA can be determined by methods well known in the art. The presence of the protein IL13Rα2 in a cancer sample or in a cell obtained from a cancer sample can be determined by methods well known in the art, for example, by means of a technique which comprises the use of antibodies with the capacity for binding specifically to IL13Rα2 (or to fragments thereof containing the antigenic determinants), or alternatively by means of a technique which does not comprise the use of antibodies such as, for example, by techniques based on mass spectroscopy.

The expression "increased expression levels" refers to an expression level of IL13Rα2 in the cancer cells higher than a reference value. In a particular embodiment, the expression level of a IL13Rα2 is considered to be higher than its reference value when it is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 120%, at least 130%, at least 140%, at least 150%, or more higher than its reference value.

The term "reference value" relates to a predetermined criteria used as a reference for evaluating the values or data obtained from the samples collected from a subject. The reference value or reference level can be an absolute value, a relative value, a value that has an upper or a lower limit, a range of values, an average value, a median value, a mean value, or a value as compared to a particular control or baseline value. A reference value can be based on an individual sample value, such as for example, a value obtained from a sample from the subject being tested, but at an earlier point in time. The reference value can be based on a large number of samples, such as from population of subjects of the chronological age matched group, or based on a pool of samples including or excluding the sample to be tested.

In a particular embodiment, when no expression of IL13Rα2 is detected, the reference value is "0".

In a particular embodiment, when IL13Rα2 expression is detected, the reference value is obtained from a sample comprising tumor cells that do not respond to the treatment with the peptide of the invention. The skilled person can determine if a tumor responds to the treatment with the peptide of the invention using the in vitro and in vivo assays described in the present application, for example, by determining the effect on the migration, invasion and proliferation of the cancer cells or by evaluating the effect on the survival of mice inoculated with the tumor cells.

In a particular embodiment, the cancer characterized by having increased expression of IL13Rα2 compared to a reference value is selected from the group consisting of colorectal cancer, glioblastoma, renal cell carcinoma, pancreatic cancer, melanoma, head and neck cancer, mesothelioma and ovarian cancer.

The term "colorectal cancer", also known as "colon cancer", "rectal cancer", or "bowel cancer", refers to a cancer from uncontrolled cell growth in the colon or rectum, or in the appendix. The term is used to refer to adenocarcinomas, carcinoid tumors, gastrointestinal stromal tumors (GISTs) or sarcomas. As used herein, the term colorectal cancer refers to stage I, stage IIA, stage IIB, stage IIC, stage IIIA, stage IIIB, stage IIIC, stage IVA or stage IVB colorectal cancer Moreover, as used herein, colorectal cancer refers both to primary colorectal tumors as well as to secondary colorectal cancer, i.e. a colorectal cancer which results from the metastasis from a primary cancer elsewhere in the body.

The term "glioblastoma", also known as "glioblastoma multiforme" or "GBM" as used, herein, refers to a type of primary brain tumor. GBM is an anaplastic, highly cellular tumor with poorly differentiated, round, or pleomorphic cells, occasional multinucleated cells, nuclear atypia, and anaplasia. Variants of the tumor include gliosarcoma, multifocal GBM, or gliomatosis cerebri (in which the entire brain may be infiltrated with tumor cells). GBM seldomly metastasizes to the spinal cord or outside the nervous system, GBM is graded by their microscopic and histological appearance. Generally, grade I (pilocytic astrocytomas) and grade II (benign astrocytomas) tumors grow slowly over many years while grade IV (GBM) grows rapidly, invading and altering brain function.

The term "renal cell carcinoma" also known as "kidney cancer" or "renal adenocarcinoma" relates to cancer wherein tumor cells are found in any tissue of the kidney including clear cell carcinomas (mixed with granular cells or not), chromophilic cancers, rhabdoid tumors of the kidney, chromophobic cancers, oncocytic cancers, collecting duct cancers, transitional cell carcinomas and sarcomatoid tumors.

The term "pancreatic cancer", as used herein, refers to refers to abnormal or un-regulated cell growth affecting the pancreas. The term "pancreatic carcinoma" includes exocrine carcinoma, endocrine carcinoma and neuroendocrine carcinoma. Illustrative non-limitative examples of pancreatic carcinoma are pancreatic adenocarcinoma, acinar cell carcinoma, cystadenocarcinomas and pancreatic mucinous cystic neoplasms. In a particular embodiment the pancreatic cancer is pancreatic ductal adenocarcinoma. "Pancreatic ductal adenocarcinoma", PDAC, as used herein, refers to a pancreatic cancer that displays a ductal-like morphology.

The term "melanoma", as used herein, refers to a malignant skin tumour of melanocytes and includes, but is not limited to, melanomas, metastatic melanomas, melanomas derived from either melanocytes or melanocyte related nevus cells, melanocarcinomas, melanoepitheliomas, melanosarcomas, melanoma in situ, superficial spreading melanoma, modular melanoma, lentigo malignant melanoma, acral lentiginous melanoma, invasive melanoma and familial atypical mole and melanoma (FAM-M) syndrome. Moreover, the term "melanoma" refers not only to primary melanomas but also to "melanoma metastasis" which, as used herein, refers to the spread of melanoma cells to regional lymph nodes and/or distant organs. This event is frequent, given that melanomas contain multiple cell populations characterized by diverse growth rates, karyotypes, cell-surface properties, antigenicity, immunogenicity, invasion, metastasis, and sensitivity to cytotoxic drugs or biologic agents. Melanoma shows frequent metastasis to brain, lungs, lymph nodes, and skin. Thus, the combinations of the invention are also useful for the treatment of melanoma metastasis.

The term "head and neck cancer", as used herein, refers to a group of biologically similar cancers that start in the upper aerodigestive tract, including the lip, oral cavity (mouth), nasal cavity (inside the nose), paranasal sinuses, pharynx, and larynx. 90% of head and neck cancers are squamous cell carcinomas (SCCHN), [1] originating from the mucosal lining (epithelium) of these regions. Head and neck squamous cell carcinomas (HNSCC's) make up the vast majority of head and neck cancers, and arise from mucosal surfaces throughout this anatomic region. These include tumors of the nasal cavities, paranasal sinuses, oral cavity, nasopharynx, oropharynx, hypopharynx, and larynx.

The term "mesothelioma" refers to a neoplasm derived from the cells lining the pleura, pericardium or peritoneoum, including but not limited to pleural mesothelioma, peritoneal mesothelioma and pericardial mesothelioma.

The term "ovarian cancer" relates to a cancerous growth arising from the ovary. As used herein, ovarian cancer is used to refer to both type I cancers (endometrioid, mucinous, and clear-cell carcinomas) as well as to type II cancers (serous carcinoma and carcinosarcoma). As used herein, ovarian cancer refers to surface epithelial-stromal tumor (adenocarcinoma), papillary serous cystadenocarcinoma, "Borderline" adenocarcinoma, adenocarcinoma, endometrioid tumor, serous cystadenocarcinoma, papillary carcinoma, mucinous cystadenocarcinoma, clear-cell ovarian tumor, mucinous adenocarcinoma, cystadenocarcinoma, sex cord-stromal tumour, Mullerian tumor, germ cell tumor, teratoma, dysgerminoma, epidermoid (squamous cell carcinoma) or Brenner tumor. As used herein, ovarian cancer refers to stage I, stage II, stage III or stage IV ovarian cancer. Moreover, as used herein, ovarian cancer refers both to primary ovarian tumors as well as to secondary ovarian cancer, i.e. an ovarian cancer which results from the metastasis from a primary cancer elsewhere in the body.

The term "asthma", as used herein, refers to inflammatory disease of the airways of the lungs. The disease is characterized by reversible airway obstruction and bronchospasm. Symptoms of the disease include episodes of wheezing, coughing, chest tightness and shortness of breath. In a particular embodiment, the asthma is allergic asthma, that is, asthma induced by allergens causing an allergic reaction. The allergens that can induce allergic asthma include some insects like cockroachs, dust miles, mold, pet urine, feces, saliva, hair or dander, pollen etc.

The term "atopic dermatitis" or "atopic eczema", as used herein, refers to an allergic skin disease typically characterized by one or more of the following signs and symptoms:
Dry skin.
Itching, which may be severe, especially at night.
Red to brownish-gray patches, especially on the hands, feet, ankles, wrists, neck, upper chest, eyelids, inside the bend of the elbows and knees, and in infants, the face and scalp.
Small, raised bumps, which may leak fluid and crust over when scratched.
Thickened, cracked, scaly skin.
Raw, sensitive, swollen skin from scratching.

The term "fibrosis", as used herein, relates to an excess deposition of extracellular matrix (ECM) involving molecular and histological re-arrangement of various types of collagens, proteoglycans, structural glycoproteins and hyaluronic acid (hyaluronan). Illustrative non-limitative examples of fibrosis include cystic fibrosis of the pancreas and lungs, injection fibrosis, which can occur as a complication of intramuscular injections, especially in children, endomyocardial fibrosis, idiopathic pulmonary fibrosis, mediastinal fibrosis, myleofibrosis, retroperitoneal fibrosis, progressive massive fibrosis, a complication of coal workers' pneumoconiosis, nephrogenic systemic fibrosis, diffuse parenchymal lung disease, post-vasectomy pain syndrome, tuberculosis (TB) can cause fibrosis of the lungs, sickle-cell anaemia may cause enlargement and ultimately fibrosis of the spleen and rheumatoid arthritis and cirrhosis, which may cause fibrosis of the liver.

The peptide, fusion protein, nanoparticle, nucleic acid, gene construct, vector, virus or viral particle, cell or pharmaceutical composition of the invention can be administered by any suitable route, for example, by oral, nasal, ocular, topical, intradermic, intracranial or intravenous route. The preferred route of administration is the oral, nasal, ocular or intradermic route.

Additional Aspects of the Invention

1. A peptide consisting of the amino acid sequence $J-X_1X_2X_3X_4X_5X_6X_7X_8$ (SEQ ID NO: 10) or its reversed sequence wherein
$X_1$ is W, F or Y,
$X_2$ is K or R,
$X_3$ is T or S
$X_4$ is I, A, L, M or V,
$X_5$ is I, L, M or V,
$X_6$ is T or S,
$X_7$ is K, A or R,
$X_8$ is N or Q, and J is a polypeptide characterized in that may or may not exist, and
if J exists is the amino acid sequence GSET (SEQ ID NO: 11) and $X_1X_2X_3X_4X_5X_6X_7X_8$ is the SEQ ID NO: 1, and
wherein said peptide is capable of inhibiting IL13/IL13Rα2 signalling.
J, according to the invention, is a peptide, preferably a peptide comprising the SEQ ID NO: 11.

2. The peptide according to aspect 1, wherein the peptide is WKTIITKN (SEQ ID NO: 1) or its reversed sequence.

3. The peptide according to aspect 1, wherein the peptide is GSETWKTIITKN (SEQ ID NO: 3) or its reversed sequence.

4. The peptide according to aspect 1, wherein the peptide has the amino acid sequence WKTAITAN (SEQ ID NO: 4) or its reversed sequence.

5. The peptide according to any one of aspects 1 to 4, wherein the peptide comprises at least one D-amino acid.

6. A fusion protein comprising a peptide according to any one of aspects 1 to 5 and at least a heterologous polypeptide.

7. A nanoparticle comprising a peptide according to any one of aspects 1 to 5 or a fusion protein according to claim 6.

8. A virus-like particle comprising a peptide according to any one of aspects 1 to 5 or a fusion protein according to claim 6.

9. A pharmaceutical composition comprising a therapeutically effective amount of a peptide according to any one of aspects 1 to 5, or a fusion protein according to aspect 6, or a nanoparticle according to aspect 7, or a virus-like particle according to aspect 8, and a pharmaceutically acceptable excipient.

10. A peptide according to any one of aspects 1 to 5, or a fusion protein according to aspect 6, or a nanoparticle according to aspect 7, or a virus-like particle according to aspect 8, or a pharmaceutical composition according to aspect 9 for use in medicine.

11. A peptide according to any one of aspects 1 to 5, or a fusion protein according to aspect 6, or a nanoparticle according to aspect 7, or a virus-like particle according to aspect 8, or a pharmaceutical composition according to aspect 9 for use in the treatment of a cancer, characterized by having increased expression of interleukin 13 receptor α2 (IL13R α2) compared to a reference value.

12. A peptide according to any one of aspects 1 to 5, or a fusion protein according to aspect 6, or a nanoparticle according to aspect 7, or a virus-like particle according to aspect 8, or a pharmaceutical composition according to aspect 9 for use in the prevention of metastatic progression in a patient suffering from a cancer characterized by having increased expression of interleukin 13 receptor α2 (IL13R α2) compared to a reference value.

13. A peptide or a fusion protein or a nanoparticle or a virus-like particle or a pharmaceutical composition for use according to any one of aspects 11 or 12, wherein the cancer is selected from the group consisting of colorectal cancer, glioblastoma, renal cell carcinoma, pancreatic cancer, melanoma, head and neck cancer, mesothelioma and ovarian cancer.

14. A peptide or a fusion protein or a virus-like particle or a nanoparticle or a nucleic acid or a gene construct or a vector or a cell or a pharmaceutical composition for use according to any one of aspects 11 to 13, wherein the metastasis is selected from the group consisting of lung, liver, brain, bone or bone marrow metastasis.

15. A peptide according to any one of aspects 1 to 5, or a fusion protein according to aspect 6, or a nanoparticle according to aspect 7, or a virus-like particle according to aspect 8, or a pharmaceutical composition according to aspect 9 for use in the treatment of asthma, atopic dermatitis or fibrosis.

The invention is described herein in more detail by way of the following examples which are to be construed as merely illustrative and not limitative of the scope of the invention.

EXAMPLES

Materials and Methods
Cell Lines, Peptides and Antibodies

Highly metastatic KM12SM and poorly metastatic KM12C human colon cancer cells were obtained directly from Dr. I. Fidler (MD Anderson Cancer Center, University of Texas, Houston, Tex.), whereas U87MG and U118MG glioblastoma cell lines were provided by Dr. G Velasco (Universidad Complutense, Madrid, Spain). SW480 and SW620 human colon cancer cell lines were purchased from the American Type Culture Collection (ATCC). All cell lines were cultured in DMEM (Invitrogen) containing 10% FCS (Invitrogen) and antibiotics at 37° C. in a 5% CO2 humidified atmosphere.

IL13Rα2 (2K8), RhoGDIα (G-2), Akt (5C10), and FAK (A-17) antibodies were purchased from Santa Cruz Biotechnology. Antibodies against pY397-FAK (#611722) and Src (AF3389) were from BD transduction laboratories and R&D systems, respectively. Antibodies against phospho-Src (#2101), phospho-Akt (#4060), ERK1/2 (L24F12) and phospho-ERK1/2 (#9101) were from Cell Signaling Technology.

Recombinant human IL13 was used at 20 ng/ml (13) and was purchased from PeproTech. IL13Rα2-derived peptides (IL13Rα2D1: GSETWKTIITKN, SEQ ID NO: 3; IL13Rα2D1S: WKTIITKN, SEQ ID NO: 1; IL13Rα2Nter: FEIVDPGY, SEQ ID NO: 14; IL13Rα2Cter WSIPLGPI, SEQ ID NO: 15; IL13Rα2D1S-1A: WATIITKN, SEQ ID NO: 16; IL13Rα2D1S-2A WKAIITKN, SEQ ID NO: 17; IL13Rα2D1S-3A WKTAITKN, SEQ ID NO: 18; IL13Rα2D1S-4A WKTIATKN, SEQ ID NO: 19; IL13Rα2D1S-5A WKTIIAKN, SEQ ID NO: 20; IL13Rα2D1S-6A WKTIITAN, SEQ ID NO: 21) were synthesized using solid phase chemistry with a Focus XC instrument (AAPPtec). The enantio version D-IL13Rα2D1 (D-D1) peptide (GSETWKTIITKN, SEQ ID NO: 3) composed entirely by D-amino acids was purchased from Proteogenix (Schiltigheim, France). Peptides were used at 1/μg/mL in the different experiments.

Biacore Assays

Binding of D1 peptide to IL-13 was monitored by surface plasmon resonance on a BIAcore 3000 instrument (BIAcore Inc, Switzerland). IL-13 was covalently amino coupled to a CM-5 sensor chip. An immobilization level of 7700 RU was obtained. A nonderivatized flow cell was used as a control. The interaction between D1 peptide and the immobilized IL13 was determined by changes in the RU at different D1 concentrations.

Cell Signaling Analysis

Cancer cells were incubated 3 h in DMEM without serum, detached with 2 mM EDTA, washed and treated with IL-13 (PeproTech) (10 ng/ml) for different times in presence or absence of IL13Rα2D1 peptide. Then, cells were lysed with lysis buffer (1% Igepal, 50 mM Tris-HCl, 100 mM NaCl, 2 mM MgCl$_2$, 10% glycerol, protease inhibitors (Complete Mini, Roche) and phosphatase inhibitor cocktails 2 and 3 (Sigma-Aldrich)). Protein extracts (60 μg) were separated in SDS-PAGE and transferred to nitrocellulose membranes, which were incubated with primary antibodies, washed and incubated with HRP-conjugated secondary antibodies (Sigma-Aldrich). Membranes were revealed using SuperSignal West Pico chemiluminescent Substrate (Thermo Scienctific).

Proliferation Assays

Cancer cells were seeded at $1 \times 10^4$ cells/well on 96-well plates and were incubated for 48 h at 37° C. in DMEM with 0.5% serum in presence of IL-13 (10 ng/ml) and the indicated peptides, followed by 1 h incubation with Thyazolyl Blue Tretrazolium Bromide (MTT) (0.6 mg/mL) (Sigma-Aldrich). Cell proliferation was determined by absorbance at 560 nm and comparison with control cells collected ab initium.

Cell Adhesion Assays

Cancer cells were starved for 3 h, labeled with BCECF-AM (Molecular Probes), detached with EDTA/PBS and incubated in DMEM in the presence of IL-13 and the indicated peptides for 10 min at 37° C. Then, $6 \times 10^4$ cells in 100 μL were added to 96-well plates previously coated with Matrigel (0.4 μg/mm$^2$), and the plates were incubated for 25 min at 37° C. Subsequently, non-adhered cells were removed by three washes with DMEM. Bound cells were lysed with 1% SDS in PBS, and the extent of the adhesion was quantified using a fluorescence analyzer (POLARstar Galaxy, BMG Labtechnologies).

Wound Healing Assays

Cancer cells were cultured to confluence in Matrigel-coated plates (0.4 μg/mm$^2$), and a 1 mm-wide wound was done across the monolayer, which was incubated in serum-free medium alone or with IL-13 (10 ng/mL), in the presence or absence of the indicated peptides. Pictures were taken immediately and after 24 h culture at 37° C. after the injury. Effective migration speed was calculated from the distance covered by cells in 24 h in each side of the wound.

Invasion Assays

For Matrigel invasion assays, $6 \times 10^4$ cells were loaded onto 8 mm pore-size filters coated with 35 mL of Matrigel (1:3 dilution; BD Biosciences) in Transwell plates (Costar) in presence of the indicated peptides. The lower compartment of the invasion chamber was filled with IL-13 (10 ng/mL). After 48 h, non-invading cells were removed from the upper surface of the filter, and cells that migrated through the filter were fixed with 4% paraformaldehyde (Sigma-Aldrich), stained with crystal violet and counted under a microscope.

Metastasis Experiments in Nude Mice

The Ethical Committee of the Consejo Superior de Investigaciones Científicas (Madrid, Spain) approved the protocols used for experimental work with mice. Swiss nude mice (Charles River) (n=5 per condition) were inoculated in the spleen with $1.5 \times 10^6$ KM12SM cells in 0.1 mL PBS in presence or absence of the indicated peptides (1 μg/mL). A day after inoculation, mice were subjected to removal of the spleen. For mice with peptide treatment, 2 days after inoculation and for 2 weeks, mice were inoculated intravenously with the indicated peptides (7 doses of 3 μg in 0.1 mL PBS). Mice were daily inspected for signs of disease, such as abdominal distension, locomotive deficit, or tumor detectable by palpation. When signs were visible, mice were euthanized, subjected to necropsy, and inspected for metastasis in liver.

For liver colonization assessment, mice were inoculated in spleen with $1 \times 10^6$ KM12SM cells, and euthanized 48 h after inoculation. RNA was isolated from liver using TRIzol (Invitrogen), retrotranscribed and 0.3 mg cDNA subjected to PCR with Taq DNA polymerase (Invitrogen) to amplify human GAPDH as previously described (13). As a control, a 20 cycle amplification of murine β-actin was performed.

Statistical Analyses

Data were analysed by one-way ANOVA followed by Tukey-Kramer multiple comparison test. Survival curves were plotted with Kaplan-Meier technique and compared with the log-rank test. The minimum acceptable level of significance in all tests was $P<0.05$.

Results

Figure 7:
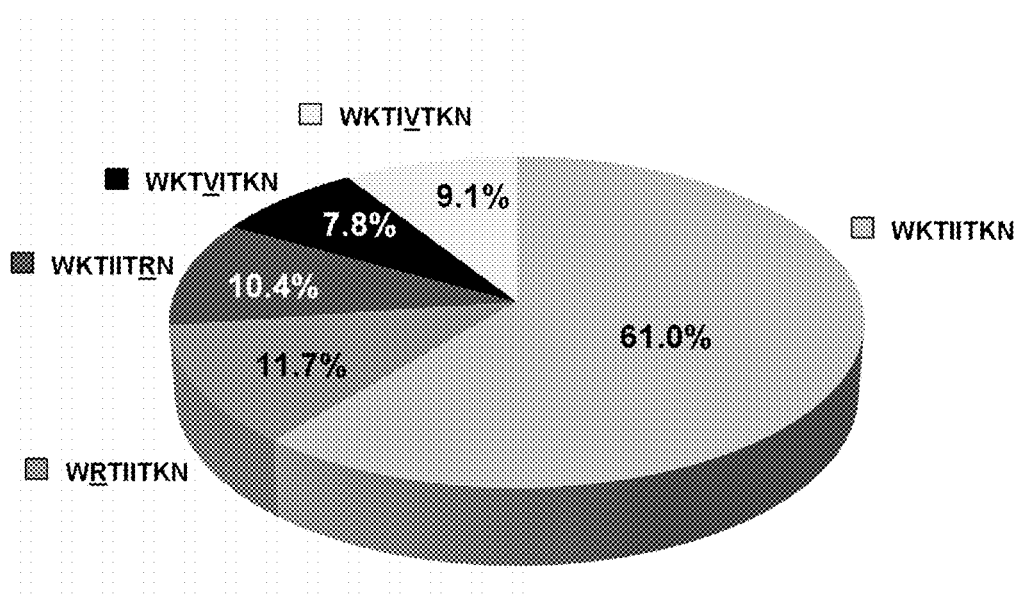
FIG. 7. The D1 peptide sequences from 77 mammal species were analyzed. The percentage of each variant in mammalians was represented in a circle graph. WKTIVTKN (SEQ ID NO: 8), WKTVITKN (SEQ ID NO: 7), WKTIITRN (SEQ ID NO: 6), WRTIITKN (SEQ ID NO: 5), WKTIITKN (SEQ ID NO: 1).

Peptide IL13Rα2 D1 Inhibits the Metastatic Capacity of Colorectal and Glioblastoma Cell Lines First, the presence of the IL13Rα2 receptor in different colorectal and glioblastoma cancer cell lines was studied (FIG. 1A). The receptor was present at different extent in all the cell lines tested, except glioblastoma T98 cells. To investigate the IL-13 blocking capacity of the IL13Rα2 D1 binding site a 12-mer peptide (GSETWKTIITKN, SEQ ID NO: 3) (D1 peptide) containing the most conserved residues of the binding site was prepared (FIG. 1B). Residues $^{81}$WKTIITKN$^{88}$ (SEQ ID NO: 1) of IL13Rα2 are highly conserved between different species, i.e. mouse sequence is WKTIITRN (SEQ ID NO: 6), suggesting a critical role in this binding site (FIG. 7). Using 20 ng/ml of IL-13 for cell activation, different amounts of D1 peptide (from 10 ng/ml to 5 µg/ml) were tested to inhibit IL-13-mediated cell adhesion in metastatic KM12SM colorectal cancer cells (FIG. 1C). A progressive increase in the IL-13 blocking capacity at the highest doses of the D1 peptide, particularly 1 and 5 µg/ml, was observed. As a balance between blocking effectivity and dose 1 µg/ml of D1 peptide was selected for the remaining experiments.

Next, the capacity of the D1 peptide to inhibit cell adhesion, migration, invasion and proliferation was examined in two colorectal cancer metastatic cell lines, KM12SM and SW620. In both cell lines, the addition of IL-13 provokes a considerable increase in adhesion, migration and invasion, and, at a lesser extent, proliferation (FIG. 2A). Whereas the addition of the peptide did not change the basal properties of the cells, the addition of the peptide to IL-13-treated cells caused a near complete inhibition of the IL-13 prometastatic effects in both colon cancer cell lines (FIG. 2A). In addition, given the reported overexpression of IL13Rα2 in glioblastoma multiforme, the capacity of the D1 peptide to inhibit the pro-metastatic capacities of IL-13 in two glioblastoma cell lines, U87 and U118, was examined (FIG. 1A). The effect of IL-13 in glioblastoma cells was different to colorectal cancer (FIG. 2B). IL-13 efficiently promoted the invasion capacity, but migration and proliferation were induced at a lesser extent and there was no effect on cell adhesion. Regardless the cell line, incubation of IL-13-treated cells with the D1 peptide abolished IL-13 effects on invasion, migration and proliferation in both glioblastoma cell lines. Collectively, these results support the notion that the administration of the D1 peptide to metastatic cell lines interferes with their metastatic properties.

Figure 3:
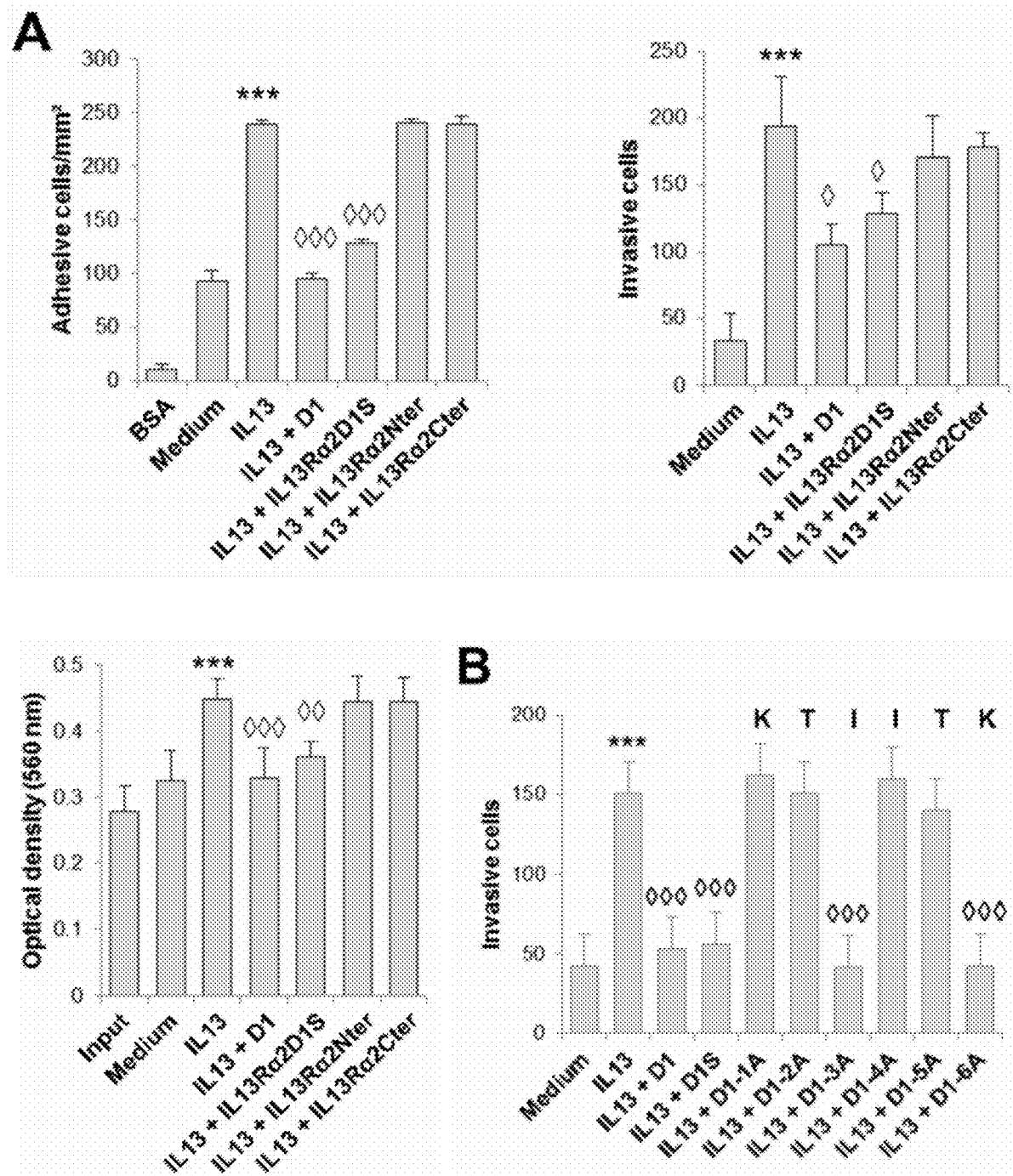
FIG. 3. Peptides derived from different regions of IL13Rα2 have different capabilities for inhibiting IL13 effects. KM12SM cells were exposed to IL13 in the presence of the indicated peptides and subjected to (A) cell adhesion assays to Matrigel, cell invasion assays through Matrigel and MTT assays. Activation of cell adhesion, invasion and proliferation was significantly enhanced by IL13 (***, p<0.001). Stimulation of cell adhesion, invasion or proliferation triggered by IL13 was inhibited by the presence of the indicated peptides (◊, p<0.05; ◊◊, p<0.01; ◊◊◊, p<0.001). (B) Ala-scanning experiment to identify residues relevant for the binding. Change of $^{84}$I and $^{87}$K by Ala did not alter the blocking capacity of the D1 peptide, indicating that these two residues are not essential for the IL-13 binding. (C) Quantitative analysis of peptide-protein interaction using Biacore assay. IL-13 was covalently amino coupled to a sensor chip CM5. Binding curves responses for D-D1 peptide were expressed in resonance units as a function of time. The kinetic parameters and concentrations of the analyte are indicated.
Figure 3:
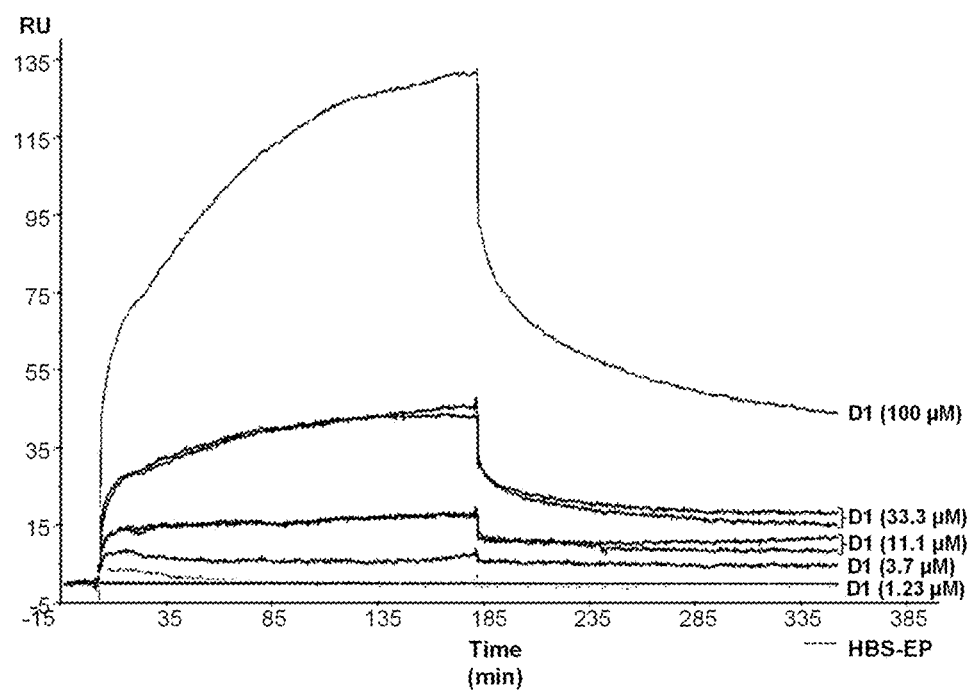

The Core Motif WKTIITKN (SEQ ID NO: 1) is Essential for Abolishing IL-13 Binding To demonstrate the specificity of the blocking effect, a shorter version of the peptide D1 containing only the core motif WKTIITKN (SEQ ID NO: 1) was tested in adhesion, invasion and proliferation of KM12SM colorectal cancer cells. In addition, two unrelated 8 amino acid peptides from the N-terminus and C-terminus of IL13Rα2 were tested to discard unspecific binding effects. Incubation of the IL-13 with the 8-mer core peptide WKTIITKN (SEQ ID NO: 1) caused similar effects to the longer 12 amino acid peptide (FIG. 3A). In contrast, unrelated peptides did not trigger any effect on adhesion, invasion and proliferation.

To identify those residues that might be more relevant for the binding, an Ala-scanning experiment was performed (FIG. 3B). Six peptides containing replacements for each of the palindromic KTIITK (SEQ ID NO: 22) residues by Ala were prepared. To study the effect of the amino acid replacements on the invasion capacity, peptides were incubated with IL-13 and added to KM12SM cells. Replacement of $^{84}$I and $^{87}$K by Ala did not alter the blocking capacity of the D1 peptide, indicating that these two residues are not essential for the IL-13 binding. Alterations of any of the other four residues caused a complete loss of the inhibitory properties. These results explain the strong conservation of this motif in the IL13Rα2 sequence.

A direct quantitative analytical method as Biacore was used to determine the affinity of the D1 peptide binding to IL-13 (FIG. 3C). Some limitations in the quantitative adjustment to the established models of the Biacore instrument caused a difficult interpretation of the results and impede an accurate determination of the affinity. The affinity range of D1 peptide binding to IL-13 was estimated to be around 100 µM.

Peptide IL13Rα2 D1 Inhibits Cell Signaling Triggered by IL-13

Figure 8:
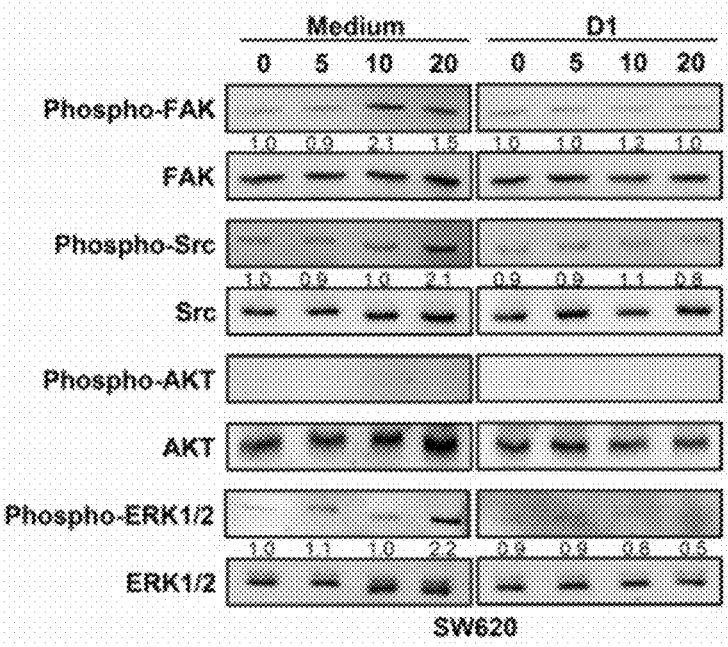
FIG. 8. D1 peptide inhibits cell signaling. SW620 (A) or U118 (B) cells were detached, resuspended in serum-free DMEM in absence or presence of D1 peptide and treated with IL13 for the indicated times. Cells were lysed, and the extracts were analyzed by Western blotting with antibodies against FAK, JNK, ERK1/2, Src and AKT, and their phosphorylated forms.
Figure 8:
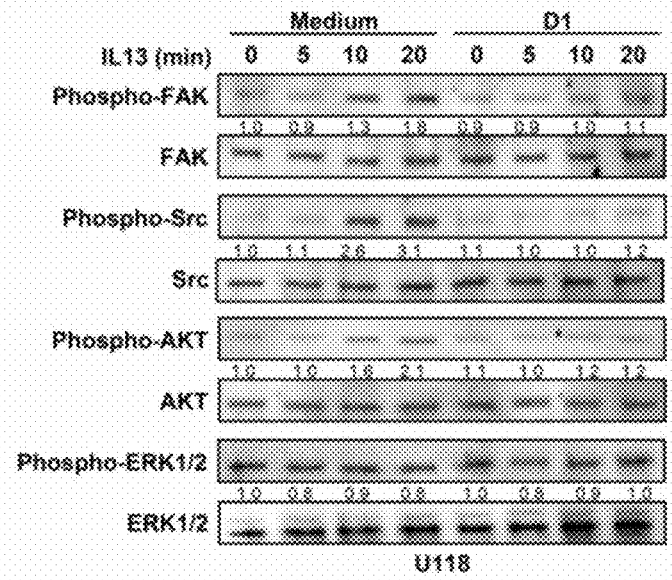

The effect of IL-13 blocking with D1 on the downstream signaling mediators in colorectal and glioblastoma cell lines was next investigated. In metastatic KM12SM colorectal cells, IL-13 addition provoked a rapid activation (5 min) of phospho-FAK and phospho-ERK1/2, followed by activation of phospho-Src and phospho-AKT at 10 min. Addition of D1 peptide caused a clear inhibition of the IL-13 cell signaling, with a significant decrease in the phosphorylation of the four downstream mediators (FAK, Src, AKT and ERK1/2) (FIG. 4A). In U87 glioblastoma cells, the results were similar to those in colorectal cancer. After incubation with IL-13 there was a fast activation of FAK, followed by Src, AKT and ERK1/2. This activation was fully blocked by addition of the D1 peptide (FIG. 4B). To corroborate these results, two additional cell lines, colorectal SW620 and glioblastoma U118, were examined. With some minor differences, overall results were quite similar (FIG. 8A, B). Together, these results demonstrate the capacity of the D1 peptide to inhibit IL-13-mediated cell signaling through FAK, Src, AKT and ERK1/2 in colorectal cancer and glioblastoma.

Synthesis of Enantiomer to Improve Peptide Stability in Blood

Figure 5:
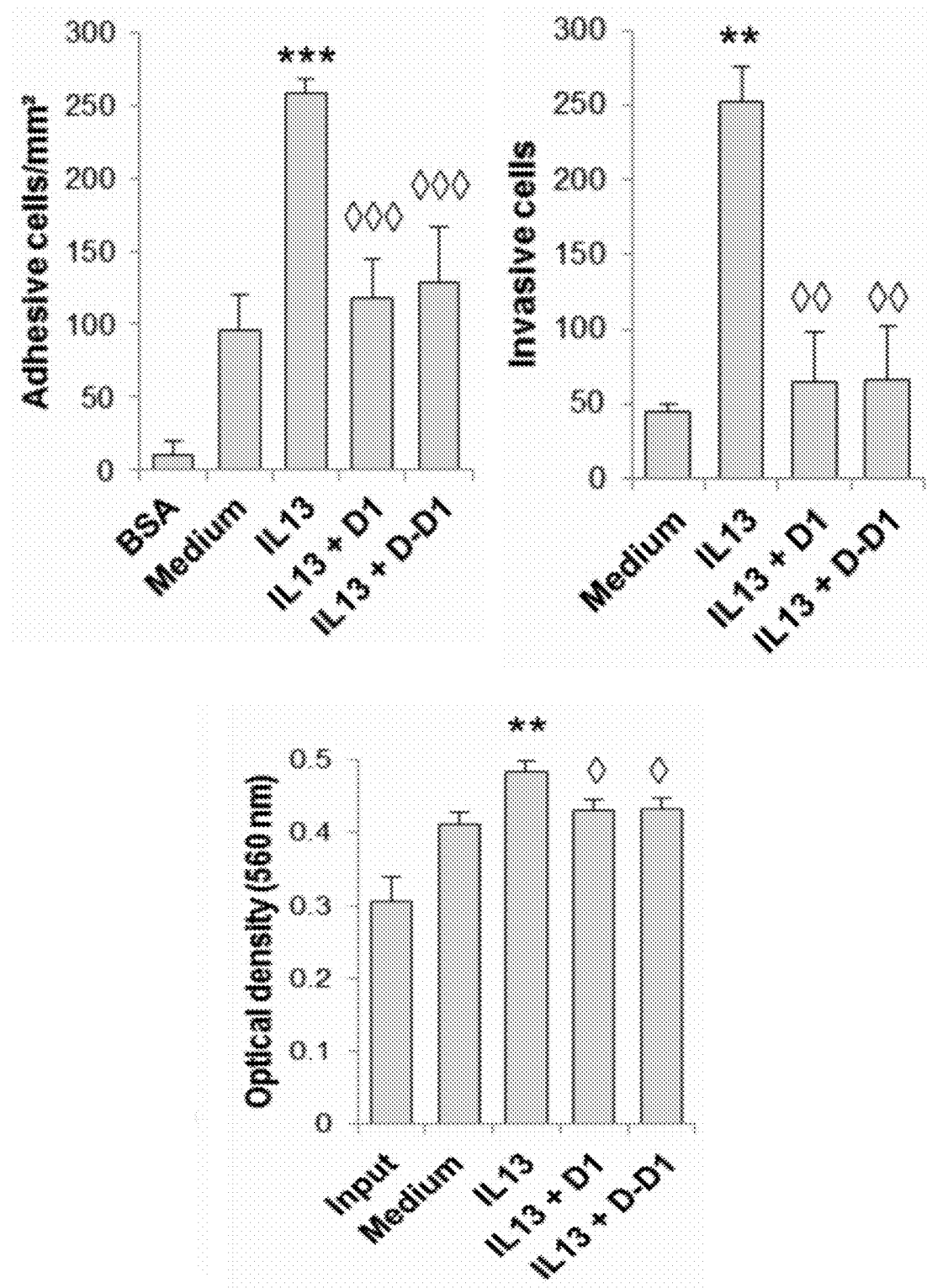
FIG. 5. Both D1 and D-D1 peptides inhibit cell adhesion, invasion and proliferation of cancer cells induced by IL-13. KM12SM cells were treated with IL13 and the indicated peptides and subjected to (A) cell adhesion assays to Matrigel, (B) cell invasion assays through Matrigel and (C) MTT assays. Cell adhesion, number of invasive or cells number of viable cells was significantly enhanced by IL13 (, p<0.01; *, p<0.001) or inhibited by the presence of the indicated peptide (◊, p<0.05; ◊◊, p<0.01; ◊◊◊, p<0.001).

One major limitation in the use of peptide-based therapies is the poor peptide stability in biological fluids. Peptides composed exclusively of natural amino acids are an easy target of multiple proteases present in the blood for proteolytic digestion. To overcome this limitation we have prepared the enantio version of the peptide consisting of D amino acids. This modification causes a considerable increase in peptide stability. To investigate the impact of this modification in the biological activity of the peptide experiments of adhesion, invasion and proliferation in KM12SM cancer cells were carried out. After incubation with IL-13, both peptides the L-version and the D-version gave similar results in the three cellular assays (FIG. 5). These results support the use of the enantio version for in vivo experiments.

Enantiomer D1 Peptide Inhibits Colorectal Cancer Metastasis and Increases Mice Survival Finally, the effect of the D1 and D-D1 peptides on the homing capacity of the KM12SM cells and the mice survival after intrasplenic inoculation of metastatic cells was investigated. For homing experiments, mice were inoculated intrasplenically with KM12SM cells treated with IL-13, D1 peptide or IL-13+D1 peptide. Spleens were removed 24 h after inoculation, to prevent the formation of tumors in spleen. Human GAPDH was used as a control gene. Mice were euthanized at 48 h after inoculation and RNA was isolated from the livers. After PCR amplification, mice treated with the D1 peptide, with or without IL-13, did not colonize the liver, as no amplification of the GAPDH gene was detected (FIG. 6A).

Next, the capacity of D1 and D-D1 peptides to delay cancer metastasis and to increase mouse survival was evaluated (FIG. 6B). Two experimental approaches were followed; either KM12SM cells were inoculated in combination with the peptide (1 µg/ml), with or without further treatment with the peptide (7 doses of 3 µg in 0.1 mL PBS). For the natural D1 peptide, there was a modest increase in survival for those mice treated with cells preincubated with the peptide but no effect was observed after treatment (FIG. 6B). In contrast, those mice inoculated with cells treated with the D-D1 peptide showed a remarkable increase in survival, with two mice surviving the experimental endpoint and no metastatic lesions at the necropsy (FIG. 6B). Mice inoculated with cells without treatment also displayed a significant increase and one surviving mice without lesions. Additionally, the capacity of the D-D1 peptide to inhibit tumour growth in U251 glioblastoma xenografts was tested. For glioblastoma xenografts, $10^7$ U251 cells were inoculated subcutaneously into the flanks of mice. Eleven days after cell inoculation, when tumours reached a size of 100 mm$^3$, mice were treated with D-D1 peptide (3 µg/100 µL of PBS) subcutaneously or with saline solution in a total of 7 doses during 15 days. Tumours were measured every 2-3 days. The results show that D-D1 peptide administration caused a significant growth arrest accompanied by a regression in the tumour size (**$p<0.01$) (FIG. 6C). These results support that the peptide administration is effective also after tumour implantation.

Collectively, these data demonstrate the therapeutic capacity of the D1 peptides to extend mice survival, with the enantiomer more than doubling the survival of the treated mice. Remarkably, survivors did not show metastatic lesions.

The invention claimed is:

1. A peptide consisting of the amino acid sequence J-$X_1X_2X_3X_4X_5X_6X_7X_8$ (SEQ ID NO: 10) or its reversed sequence wherein:
   $X_1$ is W,
   $X_2$ is K,
   $X_3$ is T,
   $X_4$ is I, A, or V,
   $X_5$ is I, or V,
   $X_6$ is T,
   $X_7$ is K, A or R,
   $X_8$ is N, and
   J may or may not exist, and
   if J exists then it is the amino acid sequence GSET (SEQ ID NO: 11), and
   wherein said peptide is capable of inhibiting IL13/IL13Rα2 signalling, and
   wherein said peptide is a synthetic peptide consisting entirely of D-amino acids.

2. The peptide according to claim 1, wherein the peptide is WKTIITKN (SEQ ID NO: 1) or its reversed sequence.

3. The peptide according to claim 1, wherein the peptide is GSETWKTIITKN (SEQ ID NO: 3) or its reversed sequence.

4. The peptide according to claim 1, wherein the peptide has the amino acid sequence WKTAITAN (SEQ ID NO: 4) or its reversed sequence.

5. A fusion protein comprising a peptide according to claim 1 fused to at least a heterologous polypeptide.

6. A nanoparticle comprising a peptide according to claim 1 or a fusion protein comprising a peptide according to claim 1 fused to at least a heterologous polypeptide.

7. A virus-like particle comprising a peptide according to claim 1 or a fusion protein comprising a peptide according to claim 1 fused to at least a heterologous polypeptide.

8. A pharmaceutical composition comprising a therapeutically effective amount of a peptide according to claim 1, or a fusion protein comprising a peptide according to claim 1 fused to at least a heterologous polypeptide, or a nanoparticle comprising a peptide according to claim 1 fused to at least a heterologous polypeptide, or a virus-like particle comprising a peptide according to claim 1 fused to at least a heterologous polypeptide, and a pharmaceutically acceptable excipient.

9. A method for the treatment of a cancer or the prevention of metastatic progression in a patient suffering from a cancer, characterized by having increased expression of interleukin 13 receptor α2 (IL13R α2) compared to a reference value, wherein the method comprising administering to a subject in need thereof the peptide of claim 1.

10. The method according to claim 9, wherein the cancer is selected from the group consisting of colorectal cancer, glioblastoma, renal cell carcinoma, pancreatic cancer, melanoma, head and neck cancer, mesothelioma and ovarian cancer.

11. The method according to claim 9, wherein the metastasis is selected from the group consisting of lung, liver, brain, bone or bone marrow metastasis.

12. A method for the treatment of asthma, atopic dermatitis or fibrosis, wherein the method comprising administering to a subject in need thereof the peptide of claim 1.

* * * * *